(12) United States Patent
Wong et al.

(10) Patent No.: US 8,703,695 B2
(45) Date of Patent: Apr. 22, 2014

(54) BIOLOGICALLY ACTIVE PEPTIDES AND THEIR NEW USES

(71) Applicants: Wai Ming Wong, Hong Kong (CN); Kong Lam, Shenzhen (CN)

(72) Inventors: Wai Ming Wong, Hong Kong (CN); Kong Lam, Shenzhen (CN)

(73) Assignee: CMS Peptides Patent Holding Company Limited, Tortola (VG)

( * ) Notice: Subject to any disclaimer, the term of this patent is extended or adjusted under 35 U.S.C. 154(b) by 0 days.

(21) Appl. No.: 13/772,357

(22) Filed: Feb. 21, 2013

(65) Prior Publication Data

US 2013/0190255 A1 Jul. 25, 2013

Related U.S. Application Data

(62) Division of application No. 13/414,686, filed on Mar. 7, 2012, which is a division of application No. 11/996,071, filed as application No. PCT/US2006/028135 on Jul. 21, 2006.

(60) Provisional application No. 60/702,542, filed on Jul. 26, 2005.

(51) Int. Cl.
*A61K 38/00* (2006.01)
*A61K 38/08* (2006.01)
*A61K 39/00* (2006.01)

(52) U.S. Cl.
USPC ........... 514/1.1; 514/5.4; 514/13.5; 514/21.6; 424/184.1; 530/300

(58) Field of Classification Search
None
See application file for complete search history.

(56) References Cited

U.S. PATENT DOCUMENTS

| | | | |
|---|---|---|---|
| 4,716,030 A * | 12/1987 | Macy | 435/14 |
| 5,382,568 A | 1/1995 | Benson | |
| 5,563,254 A | 10/1996 | Hoffman et al. | |
| 5,861,483 A | 1/1999 | Wolpe | |
| 2007/0269450 A1 | 11/2007 | Wong et al. | |

FOREIGN PATENT DOCUMENTS

| | | |
|---|---|---|
| WO | 97/35602 A1 | 10/1997 |
| WO | 98/12219 A1 | 3/1998 |
| WO | 03/006492 A2 | 1/2003 |
| WO | 2004/055042 A1 | 7/2004 |

OTHER PUBLICATIONS

Ngo et al., 1995, The Protein Folding Problem and tertiary Structure Prediction, pp. 491-495.*
Wells, Additivity of Mutational Effects in Proteins, 1990, Biochemistry, vol. 26, No. 37, pp. 8509-8517.*
Ivanov et al, Hemoglobin as a Source of Endogenous Bioactive Peptides: The Concept of Tissue-Specific Peptide Pool: Biopolymers, 1997, 43:171-188.
Fogaca et al, Antimicrobial Activity of a Bovine Hemoglobin Fragment in the Tick *Boophilus microplus*, Journal of Biological Chemistry, 1999, 274(36):25330-25334.
Karelin et al, Proteolytic Degradation of Hemoglobin in Erythrocytes Leads to Bioiogically Active Peptides, Peptides, 1995, 16(4):693-697.
Schally et al, Isolation, Structural Elucidation and Synthesis with a Tetradecapeptide with in vitro ACTH-Releasing Activity Corresponding to Residues 33-46 of the Alpha-Chain of Porcine Hemoglobin, Biochemical and Biophysical Research Communications, 1978, 82(2):582-588.
Chang et al, Isolation and Structure of Several Peptides from Porcine Hypothalami, Biochimica et Biophysica Acta, 1980, 625:266-273.
Karelin et al, Proteolytic Degradation of Hemoglobin in Erythrocytes Yields Biologically Active Peptides, Bioorganicheskaia Khimiia, 1998, 24(4):271-281.
Davis J. et al, Possible mechanisms of central nervous system fatigue during exercise, Medicine and Science in Sports and Exercise, 1997, 29:45-57.
Tanaka M. et al., Establishment and assessment of a rat model of fatigue, Meuroscience Letters, 2003, 352:159-162.
Tanaka M. et al., Mechanism of fatigue studied in a newly developed animal model of combined (mental and physical) fatigue, Fatigue Science for Human Health, 2008, 203-212.
Portenoy RK. et al., Cancer-related fatigue: guidelines for evaluation and management, The oncologist. 1999, 4:1-10.

* cited by examiner

*Primary Examiner* — Christine J Saoud
*Assistant Examiner* — Jegatheesan Seharaseyon
(74) *Attorney, Agent, or Firm* — Eagle IP Limited; Jacqueline C. Lui

(57) ABSTRACT

Novel peptides are disclosed with their use as a pharmaceutical composition. A method is also disclosed for making pharmaceutical compositions and treatment of an individual.

1 Claim, No Drawings

SEQUENCE LISTING

<160> NUMBER OF SEQ ID NOS: 21

<210> SEQ ID NO 1
<211> LENGTH: 10
<212> TYPE: PRT
<213> ORGANISM: Sus scrofa

<400> SEQUENCE: 1

Pro Thr Thr Lys Thr Tyr Phe Pro His Phe
1               5                   10

<210> SEQ ID NO 2
<211> LENGTH: 6
<212> TYPE: PRT
<213> ORGANISM: Sus  scrofa

<400> SEQUENCE: 2

Ile Val Thr Asn Thr Thr
1               5

<210> SEQ ID NO 3
<211> LENGTH: 13
<212> TYPE: PRT
<213> ORGANISM: Sus scrofa

<400> SEQUENCE: 3

Lys Ala Val Gly His Leu Asp Asp Leu Pro Gly Ala Leu
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetically prepared peptide sequence

<400> SEQUENCE: 4

Pro Thr Thr Lys Thr Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetically prepared peptide sequence

<400> SEQUENCE: 5

Pro Thr Thr Lys Thr Tyr Phe Pro
1               5

<210> SEQ ID NO 6

<400> SEQUENCE: 6

000

<210> SEQ ID NO 7
<211> LENGTH: 12
<212> TYPE: PRT
<213> ORGANISM: Sus scrofa

<400> SEQUENCE: 7

Ala Ala His His Pro Asp Asp Phe Asn Pro Ser Val
1               5                   10

```
<210> SEQ ID NO 8
<211> LENGTH: 3
<212> TYPE: PRT
<213> ORGANISM: Artificial
<220> FEATURE:
<223> OTHER INFORMATION: Synthetically prepared peptide sequence
<220> FEATURE:
<221> NAME/KEY: MOD_RES
<222> LOCATION: (3)..(3)
<223> OTHER INFORMATION: Xaa = Nle (Norleucine)

<400> SEQUENCE: 8

Tyr Ser Xaa
1

<210> SEQ ID NO 9
<211> LENGTH: 3
<212> TYPE: PRT
<213> ORGANISM: Artificial Sequence
<220> FEATURE:
<223> OTHER INFORMATION: Synthetically prepared peptide sequence

<400> SEQUENCE: 9

Tyr Thr Val
1

<210> SEQ ID NO 10
<211> LENGTH: 3
<212> TYPE: PRT
<213> ORGANISM: Artificial Sequence
<220> FEATURE:
<223> OTHER INFORMATION: Synthetically prepared peptide sequence
<220> FEATURE:
<221> NAME/KEY: MOD_RES
<222> LOCATION: (1)..(1)
<223> OTHER INFORMATION: Xaa = 3,5 - dibromo-tyrosine

<400> SEQUENCE: 10

Xaa Ser Leu
1

<210> SEQ ID NO 11
<211> LENGTH: 3
<212> TYPE: PRT
<213> ORGANISM: Artificial Sequence
<220> FEATURE:
<223> OTHER INFORMATION: Synthetically prepared peptide sequence

<400> SEQUENCE: 11

Leu Tyr Ser
1

<210> SEQ ID NO 12

<400> SEQUENCE: 12

000

<210> SEQ ID NO 13

<400> SEQUENCE: 13

000

<210> SEQ ID NO 14

<400> SEQUENCE: 14
```

```
-continued

000

<210> SEQ ID NO 15
<211> LENGTH: 3
<212> TYPE: PRT
<213> ORGANISM: Sus scrofa

<400> SEQUENCE: 15

Ala Ala Phe
1

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21
<211> LENGTH: 4
<212> TYPE: PRT
<213> ORGANISM: Sus scrofa

<400> SEQUENCE: 21

Phe Glu Glu Met
1
```

BIOLOGICALLY ACTIVE PEPTIDES AND THEIR NEW USES

BACKGROUND OF THE INVENTION

1. Field of the Invention

The present invention is related to short peptides and the use thereof. In particular, the present invention is related to short peptides with biological activities.

2. Description of the Related Art

Peptides are known in the art for treatment of diseases and as pharmaceutical compositions. For example, U.S. Pat. No. 6,191,113 discloses a peptide that has inhibitory activity for the growth of smooth muscle cells and is therefore useful for preventing and treating pathological conditions associated with growth of smooth muscle cells such as arteriosclerosis, restenosis after angioplasty, luminal stenosis after grafting blood vessel and smooth muscle sarcoma. U.S. Pat. No. 6,184,208 discloses another peptide that is found to modulate physiological processes such as weight gain activity of the epithelial growth zone and hair growth. Furthermore, PCT publication No. WO 03/006492 and U.S. patent application Ser. No. 10/237,405 suggested that certain peptides and their pharmaceutical compositions are biologically active and capable of modulating immune responses.

It is therefore an object of the present invention to provide a short peptide or peptides that have biological activity.

SUMMARY OF THE INVENTION

The peptides according to the present invention were individually synthesized by standard chemical methods. Using known animal and in vitro methods, various biological functions of these peptides were analyzed using methods described in the following references as described below. The peptide names are given the code "CMS" followed by a number. The peptide sequence and the corresponding ID numbers are shown in Table 1. A total of 7 new peptides have been identified as having in vivo biological activities, and indicated with an asterisk next to the sequence ID Number. The remaining peptides have been reported previously in WIPO publication WO 03/006492, but novel and inventive new indications have been found in the present invention. For ease of reference, the sequences that are found in WO 03/006492 have been given the same sequence ID number.

TABLE 1

| Sequence Listing ID No. | Peptide Name | Peptide Sequence |
|---|---|---|
| 1 | CMS-001 | Pro Thr Thr Lys Thr Tyr Phe Pro His Phe |
| 2 | CMS-017 | Ile-Val-Thr-Asn-Thr-Thr |
| 3 | CMS-008 | Lys Ala Val Gly His Leu Asp Asp Leu Pro Gly Ala Leu |
| 4* | CMS001.30 | Pro-Thr-Thr-Lys-Thr-Tyr |
| 5* | CMS001.31 | Pro-Thr-Thr-Lys-Thr-Tyr-Phe-Pro |
| 6 | | No sequence |
| 7 | CMS-014 | Ala Ala His His Pro Asp Asp Phe Asn Pro Ser Val |
| 8* | CMS024.04 | Tyr-Ser-Nle where Nle = norleucine (2-aminohexanoic acid) |
| 9* | CMS024.05 | Tyr-Thr-Val |
| 10* | CMS024.14 | (3,5-dibromo-Tyr)-Ser-Leu |
| 11* | CMS024.16 | Leu-Tyr-Ser |
| 12 | | No sequence |
| 13 | | No sequence |
| 14 | | No sequence |
| 15 | CMS-023 | Ala Ala Phe |

TABLE 1-continued

| Sequence Listing ID No. | Peptide Name | Peptide Sequence |
|---|---|---|
| 16 | | No sequence |
| 17 | | No sequence |
| 18 | | No sequence |
| 19 | | No sequence |
| 20 | | No sequence |
| 21 | CMS-030 | Phe Glu Glu Met |

Accordingly, one aspect of the present invention relates to substantially pure peptides having sequences identified as SEQ ID Nos. 4, 5, 8-11. Thus the present invention also relates to a substantially pure peptide comprising an amino acid sequence selected from the group consisting of SEQ ID Nos. 4, 5, 8-11. It also relates to a substantially pure peptide consisting essentially of an amino acid sequence selected from the group consisting of SEQ ID Nos. 4, 5, 8-11. The invention also relates to a substantially pure peptide consisting of an amino acid sequence selected from the group consisting of SEQ ID Nos. 4, 5, 8-11. In a specific embodiment, the peptides can modulate, but are not limited to modulating, one or more of the following: fatigue, nutritional disorders, metabolic disorders, lipid metabolism disorder, acidosis, immune activity, effects of radiation, hepatitis, rejection of transplanted organ, the growth of cancer and appetite.

In the more preferred embodiment, the peptides can modulate, but are not limited to modulating one or more of the following conditions: liver glycogen storage, blood lactic acid levels, radiotherapy-induced immunodeficiency, hepatitis B infection, skin graft rejection, liver cancer, stomach cancer, inflammation, blood lipid, triglyceride and total cholesterol, immune hypersensitivity, T-lymphocyte proliferation, mixed lymphocyte proliferation, obesity, and higher than normal body weight.

Another aspect of the present invention relates to substantially pure peptides that are functional derivatives of peptides having sequences identified as sequence ID No. 4, 5, 8-11. Thus the present invention relates also to a substantially pure peptide comprising an amino acid sequence which is a functional derivative of a biologically active peptide, this biologically active peptide having an amino acid sequence selected from the group consisting of SEQ ID Nos. 4, 5, 8-11. It also relates to a substantially pure peptide consisting essentially of an amino acid sequence which is a functional derivative of a biologically active peptide, this biologically active peptide having an amino acid sequence selected from the group consisting of SEQ ID Nos. 4, 5, 8-11. The invention also relates to a substantially pure peptide consisting of an amino acid sequence which is a functional derivative of a biologically active peptide, this biologically active peptide having an amino acid sequence selected from the group consisting of SEQ ID Nos. 4, 5, 8-11. In a specific embodiment, the peptides that are functional derivatives can modulate, but not limited to modulating, one or more of the following: fatigue, nutritional disorders, metabolic disorders, lipid metabolism disorder, acidosis, immune activity, effects of radiation, hepatitis, rejection of transplanted organ, the growth of cancer and appetite.

Another aspect of the present invention relates to a genetic vector comprising a nucleotide sequence encoding a peptide comprising an amino acid sequence selected from the group consisting of a peptide comprising one of SEQ ID Nos. 4, 5, 8-11. It also relates to a genetic vector comprising a nucleotide sequence encoding a peptide consisting essentially of an amino acid sequence selected from the group consisting of a peptide comprising SEQ ID Nos. 4, 5, 8-11. The invention also relates to a genetic vector comprising a nucleotide sequence encoding a peptide comprising a functional derivative of a biologically active amino acid sequence selected from the group consisting of SEQ ID Nos. 4, 5, 8-11. It also relates to a genetic vector comprising a nucleotide sequence encoding a peptide consisting essentially of an amino acid sequence which is a functional derivative of a biologically active amino acid sequence selected from the group consisting of SEQ ID Nos. 4, 5, 8-11.

Yet another aspect of the present invention relates to hybrid peptides containing a leader peptide adjacent a peptide, the peptide comprising, consisting essentially of, or consisting of an amino acid sequence selected from the group consisting of SEQ ID Nos. 4, 5, 8-11. The present invention also relates to hybrid peptides containing a leader peptide adjacent a peptide, the peptide comprising a functional derivative of a biologically active peptide, this biologically active peptide comprising, consisting essentially of, or consisting of an amino acid sequence selected from the group consisting of SEQ ID Nos. 4, 5, 8-11.

The present invention also relates to a genetic vector comprising a nucleotide sequence encoding a peptide comprising a leader amino acid sequence adjacent to a peptide comprising an amino acid sequence which is a functional derivative of a biologically active amino acid sequence selected from the group consisting of SEQ ID Nos. 4, 5, 8-11. It also relates to a genetic vector comprising a nucleotide sequence encoding a peptide comprising a leader amino acid sequence adjacent to a nucleotide sequence encoding a peptide consisting essentially of an amino acid sequence which is a functional derivative of a biologically active amino acid sequence selected from the group consisting of SEQ ID Nos. 4, 5, 8-11.

In a specific embodiment, the peptides produced in any of the above-described genetic vectors can modulate, but are not limited to modulating, one or more of the following: fatigue, nutritional disorders, metabolic disorders, lipid metabolism disorder, acidosis, immune activity, effects of radiation, hepatitis, rejection of transplanted organ, the growth of cancer and appetite.

Yet another aspect of the present invention relates to a micro-organism with a genome comprising a nucleotide sequence encoding a peptide comprising an amino acid sequence selected from the group consisting of SEQ ID Nos. 4, 5, 8-11. It also relates to a micro-organism with a genome comprising a nucleotide sequence encoding a peptide consisting essentially of an amino acid sequence selected from the group consisting of SEQ ID Nos. 4, 5, 8-11.

Yet another aspect of the present invention relates to a micro-organism with genetic material comprising a nucleotide sequence encoding a peptide, preferably an exogenous peptide comprising an amino acid sequence which is a functional derivative of a biologically active amino acid sequence selected from the group consisting of SEQ ID Nos. 4, 5, 8-11. It also relates to a micro-organism with a genetic composition comprising a nucleotide sequence encoding an exogenous peptide consisting essentially of an amino acid sequence which is a functional derivative of a biologically active amino acid sequence selected from the group consisting of SEQ ID Nos. 4, 5, 8-11. Exogenous peptide as used herein refers to a peptide having an amino acid sequence that is different from any other peptides normally expressed by the micro-organism in its natural, unmodified form.

Yet another aspect of the present invention relates to a micro-organism with a genetic composition comprising a nucleotide sequence encoding a peptide, preferably an exogenous hybrid peptide comprising a leader amino acid sequence adjacent a peptide, the peptide comprising an amino acid sequence selected from the group consisting of SEQ ID Nos. 4, 5, 8-11. It also relates to a micro-organism with a genome comprising a nucleotide sequence encoding a hybrid peptide comprising a leader amino acid sequence adjacent to a peptide consisting essentially of or consisting of an amino acid sequence selected from the group consisting of SEQ ID Nos. 4, 5, 8-11.

Yet another aspect of the present invention relates to a micro-organism with a genetic composition comprising a nucleotide sequence encoding an exogenous hybrid peptide comprising a leader amino acid sequence adjacent to a peptide, the peptide comprising an amino acid sequence which is a functional derivative of a biologically active amino acid sequence selected from the group consisting of SEQ ID Nos. 4, 5, 8-11. It also relates to a micro-organism with a genetic composition comprising a nucleotide sequence encoding an exogenous hybrid peptide comprising a leader amino acid sequence adjacent a peptide consisting essentially of or consisting of an amino acid sequence which is a functional derivative of a biologically active amino acid sequence selected from the group consisting of SEQ ID Nos. 4, 5, 8-11.

In a specific embodiment, the peptides produced in any of the above-described micro-organism can modulate, but are not limited to modulating, one or more of the following: fatigue, nutritional disorders, metabolic disorders, lipid metabolism disorder, acidosis, immune activity, effects of radiation, hepatitis, rejection of transplanted organ, the growth of cancer and appetite.

Yet another aspect of the present invention relates to a pharmaceutical composition comprising a substantially pure peptide comprising an amino acid sequence selected from the group consisting of SEQ ID Nos. 4, 5, 8-11. The invention also relates to pharmaceutical composition comprising a substantially pure peptide consisting essentially of or consisting of an amino acid sequence selected from the group consisting of SEQ ID Nos. 4, 5, 8-11.

The present invention also relates to a pharmaceutical composition comprising a substantially pure peptide comprising a functional derivative of a biologically active peptide, this biologically active peptide comprising an amino acid sequence selected from the group consisting of SEQ ID Nos. 4, 5, 8-11. It also relates to a pharmaceutical composition comprising a substantially pure peptide consisting essentially of a functional derivative of a biologically active peptide, this biologically active peptide having an amino acid sequence selected from the group consisting of SEQ ID Nos. 4, 5, 8-11. It further relates to pharmaceutical composition comprising a substantially pure peptide consisting of functional derivative of a biologically active peptide, this biologically active peptide having an amino acid sequence selected from the group consisting of SEQ ID Nos. 4, 5, 8-11.

In a specific embodiment, the peptides present in any of the above-described pharmaceutical compositions can modulate, but not limited to modulating, one or more of the following: fatigue, nutritional disorders, metabolic disorders, lipid metabolism disorder, acidosis, immune activity, effects of radiation, hepatitis, rejection of transplanted organ, the growth of cancer and appetite.

Yet a further aspect of the present invention relates to a method of making a pharmaceutical composition comprising providing a substantially pure peptide comprising an amino acid sequence selected from the group consisting of SEQ ID Nos. 4, 5, 8-11; and admixing said substantially pure peptide with a pharmaceutically acceptable carrier. It also relates to a method of making a pharmaceutical composition comprising providing a substantially pure peptide consisting essentially of or consisting of an amino acid sequence selected from the group consisting of SEQ ID Nos. 4, 5, 8-11 and admixing said substantially pure peptide with a pharmaceutically acceptable carrier.

Another aspect of the present invention is a method of making a pharmaceutical composition comprising providing a substantially pure peptide comprising an amino acid sequence which is a functional derivative of a biologically active peptide, this biologically active peptide having an amino acid sequence selected from the group consisting of SEQ ID Nos. 4, 5, 8-11; and mixing said substantially pure peptide with a pharmaceutically acceptable carrier.

It further relates to a method of making a pharmaceutical composition comprising providing a substantially pure peptide consisting essentially of or consisting of an amino acid sequence which is a functional derivative of a biologically active peptide, this biologically active peptide having an amino acid sequence selected from the group consisting of SEQ ID Nos. 4, 5, 8-11; and mixing the substantially pure peptide with a pharmaceutically acceptable carrier.

In connection with any of the above-described method, the peptide can modulate, but is not limited to modulating, one or more of the following: immune activity, fatigue, nutritional disorders, metabolic disorders, lipid metabolism disorder, acidosis, immune activity, effects of radiation, hepatitis, rejection of transplanted organ, the growth of cancer and appetite.

Yet a further aspect of the present invention relates to a method of treatment of a human comprising administering a pharmaceutically effective dose of a substantially pure peptide comprising, consisting essentially of, or consisting of an amino acid sequence selected from the group consisting of SEQ ID Nos. 4, 5, 8-11 to a human. It also relates to a method of treatment of a human comprising administering a pharmaceutically effective dose of a substantially pure peptide comprising, consisting essentially of, or consisting of an amino acid sequence which is a functional derivative of a biologically active peptide, this biologically active peptide having an amino acid sequence selected from the group consisting of SEQ ID Nos. 4, 5, 8-11.

In a specific embodiment, the peptides used for the treatment of human described above may be used to modulate, but are not limited to modulating, one or more of the following human conditions: fatigue, nutritional disorders, metabolic disorders, lipid metabolism disorder, acidosis, immune activity, effects of radiation, hepatitis, rejection of transplanted organ, the growth of cancer and appetite.

In connection with any of the above-described nucleic acid sequences, the peptides and/or hybrid peptides expressed from these nucleic acid sequences can modulate, but are not limited to modulating, the following: fatigue, nutritional disorders, metabolic disorders, lipid metabolism disorder, acidosis, immune activity, effects of radiation, hepatitis, rejection of transplanted organ, the growth of cancer and appetite.

In yet another aspect, the present invention relates to the use of a biologically active peptide, said biologically active peptide having an amino acid sequence comprising, consisting essentially of, or consisting of an amino acid sequence selected from the group consisting of SEQ ID No. 1, 2, 15 or functional derivatives thereof in the manufacture of a medicament for modulating at least one of the following conditions: hepatitis, fatigue, liver glycogen storage level, blood lactic acid level and immune reaction of an individual. It also relates to a method of modulating hepatitis, liver glycogen storage level, blood lactic acid level or immune reaction of an individual comprising administering a pharmaceutically effective dose of a biologically active peptide, said biologically active peptide having an amino acid sequence consisting essentially of an amino acid sequence selected from the group consisting of SEQ ID No. 1, 2, 15 or functional derivatives thereof.

The present invention further relates to the use of a biologically active peptide, said biologically active peptide having an amino acid sequence comprising, consisting essentially of, or consisting of an amino acid selected from the group consisting of SEQ ID No. 3, 7 or 21 or functional derivatives thereof in the manufacture of a medicament for modulating at least one of the following conditions: fatigue inflammation, appetite, body weight, body fat, blood lipid level, blood triglyceride level, blood cholesterol level, inflammation and immunity. The present invention also relates to a method of modulating at least one of the following conditions: fatigue inflammation, appetite, body weight, body fat, blood lipid level, blood triglyceride level, blood cholesterol level, inflammation and immunity in an individual comprising administering a pharmaceutically effective dose of a biologically active peptide, said biologically active peptide having an amino acid sequence comprising, consisting essentially of, or consisting of an amino acid sequence selected from the group consisting of SEQ ID No. 3, 7 or 21 or functional derivatives thereof.

A further aspect of the present invention is directed to a nutritional composition containing the peptide comprising, consisting essentially of or consisting of an amino acid selected from the group consisting of SEQ ID Nos. 4, 5, 8-11 or functional derivatives thereof and the use of the same for the manufacture of a nutritional supplement.

In a further aspect of the present invention, enhanced derivatives of the peptide of SEQ ID Nos. 4, 5, 8-11 and functional derivatives thereof are provided. Enhanced derivatives of these peptides comprise an enhancement molecule operably linked to these peptides in such a manner as to improve or augment the therapeutic effectiveness of the peptide. The enhancement effect may be that of a prolonged effect, a shortened effect, a delayed onset of effect, a hastened onset of effect, an increased intensity of effect, a decreased intensity of effect, a reduction in side effects, the creation of one or more effects, a delayed subsiding of effect, a hastened subsiding of effect and a targeting of the peptide to a discrete location within an individual. Examples of such enhancement molecules and enhanced derivatives are described below. In some aspects of the invention, the enhanced molecules can treat or prevent, but are not limited to treating or preventing, viral infections and immunological disorders. Additional aspects of the present invention include methods of enhancing the therapeutic effects of a peptide comprising, consisting essentially of or consisting of a peptide selected from the group consisting of SEQ ID Nos. 4, 5, 8-11 and their derivatives, comprising operably linking said peptide to a molecule which enhances the therapeutic effect. In some aspects of the invention, said operably linked molecule which enhances the therapeutic effect is not a peptide that is adjacent to a peptide selected from the group consisting of SEQ ID Nos. 4, 5, 8-11 and their derivatives in a naturally occurring peptide.

In a further aspect of the invention, a composition comprising a substantially pure peptide comprising, consisting essentially of, or consisting of an amino acid sequence selected from the group consisting of SEQ ID Nos. 4, 5, 8-11 is provided.

In an additional aspect of the invention, a method of reducing the effects of a human disease is provided, by administering a pharmaceutically effective dose of a biologically active peptide comprising, consisting essentially of, or consisting of an amino acid sequence selected from the group consisting of SEQ ID Nos. 4, 5, 8-11. In some embodiments, the human suffers from at least one of the following conditions: fatigue, nutritional disorders, metabolic disorders, lipid metabolism disorder, acidosis, immune activity, effects of radiation, hepatitis, rejection of transplanted organ, the growth of cancer and appetite.

In a further aspect of the invention, a method of modulating or treating a condition comprising administering a biologically active peptide having an amino acid sequence comprising, consisting essentially of, or consisting of essentially of SEQ ID No. 1 or a functional derivative thereof is provided, wherein the condition is selected from the group consisting of: fatigue, liver glycogen storage level, blood lactic acid level and immune reaction of an individual.

In an additional aspect of the invention, a method of modulating liver glycogen storage level, blood lactic acid level or immune reaction of an individual is provided, by administering a pharmaceutically effective dose of a biologically active peptide comprising, consisting essentially of, or consisting of an amino acid sequence comprising, consisting essentially of, or consisting of essentially of SEQ ID No. 1 or a functional derivatives thereof.

In a yet further aspect of the invention, a biologically active peptide is provided, having an amino acid sequence comprising, consisting essentially of, or consisting of an amino acid sequence selected from the group consisting of SEQ ID No. 2 or 15 or functional derivatives thereof in the manufacture of a medicament for the treatment of hepatitis.

In a yet further aspect of the invention, a method of treating hepatitis in an individual is provided, by administering a pharmaceutically effective dose of a biologically active peptide, the biologically active peptide having an amino acid sequence comprising, consisting essentially of, or consisting of an amino acid sequence selected from the group consisting of SEQ ID No. 2 or 15 or functional derivatives thereof.

In an additional aspect of the invention, a biologically active peptide is provided, having an amino acid sequence comprising, consisting essentially of, or consisting of SEQ ID No. 3 or functional derivatives thereof in the manufacture of a medicament for the alleviation of fatigue.

In a further aspect of the invention, a method of alleviating fatigue in an individual is provided, by administering a pharmaceutically effective dose of a biologically active peptide having an amino acid sequence comprising, consisting essentially of, or consisting of SEQ ID No. 3 or functional derivatives thereof.

In a yet further aspect of the invention, the use of a biologically active peptide is provided, having an amino acid sequence comprising, consisting essentially of, or consisting of SEQ ID No. 21 or functional derivatives thereof in the manufacture of a medicament for modulating at least one of the following conditions: inflammation, appetite, body weight, body fat, blood lipid level, blood triglyceride level, blood cholesterol level, inflammation and immunity.

In a yet further aspect of the invention, a method of modulating at least one of the following conditions is provided: inflammation, appetite, body weight, body fat, blood lipid level, blood triglyceride level, blood cholesterol level, inflammation and immunity in an individual comprising administering a pharmaceutically effective dose of a biologically active peptide, the biologically active peptide having an amino acid sequence comprising, consisting essentially of, or consisting of SEQ ID No. 21 or functional derivatives thereof.

In a further aspect of the invention, the use of a biologically active peptide is provided, having an amino acid sequence comprising, consisting essentially of, or consisting of SEQ ID No. 7 or functional derivatives thereof in the manufacture of a medicament for modulating the immune system of an individual.

In a yet further aspect of the invention, a method of modulating the immune system of an individual is provided, by administering a pharmaceutically effective dose of a biologically active peptide having an amino acid sequence comprising, consisting essentially of, or consisting of SEQ ID No. 7 or functional derivatives thereof.

DETAILED DESCRIPTION OF THE PREFERRED EMBODIMENT

As described herein, peptides described herein have been found to have important biological activities. The peptides can be readily synthesized by standard synthetic methods from L-amino acids, but may also be synthesized by genetic engineering methods using nucleic acids that have sequences encoding the individual peptides. All references cited are incorporated herein in their entirety.

As used herein, "substantially pure peptide" refers to peptides that are at least 40% and more preferably 60% and more preferably more than 90% pure. In the most preferred embodiment, the purity is about 99%-100%. The substantially pure peptide can be used to prepare pharmaceutical and nutritional formulations that may be complex mixtures as described below.

As used herein, the term "hybrid peptide" is used to refer to peptides that contain additional peptides inserted into the original biologically active peptide described herein having the sequence specified above or its functional derivatives, but still retain substantially similar activity. The additional peptides include leader peptides that contain, for example, an amino acid sequence that is recognized by one or more prokaryotic or eukaryotic cells as a signal for secretion of the hybrid protein to the exterior of the cell. The secretion may be a direct secretion, or indirectly through secretory vesicles.

As described above, another embodiment of the present invention is a peptide or polypeptide consisting essentially of a peptide of the present invention. As used herein, the terminology "consisting essentially of" refers to a peptide or polypeptide which includes the amino acid sequence of the peptides of the present invention along with additional amino acids at the carboxyl and/or amino terminal ends and which maintains the activity of the peptides of the present invention provided herein. Thus, as a non-limiting example, where the activity of the peptide of the present invention is to modulate immune activity, a peptide or polypeptide "consisting essentially of" the peptide of the present invention will possess the activity of modulating immune activity as provided herein with respect to that peptide and will not possess any characteristics which materially reduces the ability of the peptide or polypeptide to modulate immune activity or which constitutes a material change to the basic and novel characteristics of the peptide as a modulator of immune activity. Thus, in the foregoing example, a full length naturally occurring polypeptide which has a primary activity other than modulating immune activity and which contains the amino acid sequence of a peptide of the present invention somewhere therein would not constitute a peptide or polypeptide "consisting essentially of" a peptide of the present invention Likewise, in the foregoing example, a genetically engineered peptide or polypeptide which has a primary activity other than modulating immune activity but includes the amino acid sequence of a peptide of the present invention somewhere therein would not constitute a peptide or polypeptide "consisting essentially of" a peptide of the present invention.

In the preferred embodiment, the terminology "consisting essentially of" refer to peptides or polypeptides which have 4 or less amino acids in addition to one of the peptide of the present invention. In the more preferred embodiment, the same terminology refers to peptides or polypeptides with 2 amino acids in addition to one of the peptide of the present invention. In the most preferred embodiment, the same terminology refers to peptides or polypeptides with one amino acid in addition to one of the peptide of the present invention.

Besides the example of immune activity modulation used for illustration above, the foregoing definition also applies to all the peptides of the present invention with respect to the activities provided for such peptides. In particular, the foregoing definition applies to peptides of the invention having activities in modulating fatigue, nutritional disorders, metabolic disorders, lipid metabolism disorder, acidosis, immune activity, effects of radiation, hepatitis, rejection of transplanted organ, the growth of cancer and appetite.

Those skilled in the art can readily determine whether a peptide or polypeptide consists essentially of a peptide of the present invention under the foregoing definitions by measuring the activity of the peptide or polypeptide using the assays as described below.

Those skilled in the art can readily determine whether a peptide or polypeptide consists essentially of a peptide of the present invention under the foregoing definitions by measuring the activity of the peptide or polypeptide using the assays for modulation of disorders such as fatigue, nutritional disorders, metabolic disorders, lipid metabolism disorder, acidosis, immune activity, effects of radiation, hepatitis, rejection of transplanted organ, the growth of cancer and appetite which are provided herein with respect to a particular peptide of the present invention.

The terminology "disorder" as used herein and in the claims refers to any conditions in the body that fall outside the normal range as measured by standard methods. For example, in humans, "lipid metabolism disorder" refer to a condition in which any of the lipid levels in the body exceeds the normal range for that particular person based on the gender, height and age, as determined by standard medical diagnostic tests.

The peptide may be administered by any suitable route. Example administration routes are by intravenous injection, intramuscular injection, intraperitoneal injection, subcutaneous injection, and subcutaneous implantation, with or without delivery facilitating device such as liposome, sustain release protection, and the like. Thus the present invention includes devices for injecting the peptide into a subject. In some embodiments the device may be a syringe. The peptide may also be administered in any form of oral administration. Examples may include but are not limited to like tablet, capsule, suspension, solution, a lozenge, and the like, in the usual form without modification or in a slow release form, or with or without gastro-enteric protection. The peptide may further be applied in any form of topical application such as an ointment, cream, gel etc with or without transdermal facilitating device, or as inhalant of powder, dissolved, or as liposome protected form.

It is understood that it may be possible to add additional amino acids to the amino or carboxyl termini of the disclosed peptides described herein as another method of practicing the present invention. For example, one or two amino acids may be added to the disclosed peptide without affecting its biological function. It may also be possible to add three or four amino acids and still maintain the function of the peptides. These are all referred to as variants of the same peptide. Alternatively, one or two amino acids may be deleted from the peptide without affecting its biological activity. It may further be possible for three or four amino acids to be deleted without affecting the biological function of the peptides. These are referred to as fragments of the instant peptide. Furthermore, derivatives of the peptide such as conservative replacement of one amino acid for another within the same functional class may be used to practise another aspect of the present invention. For example, peptides having non-polar or hydrophobic side chains may be possible to substitute one side group for another without reducing biological activity. As a further example, a linker/spacer may be inserted into the peptide to form variants, but the variants still retaining its active moiety as the original peptide used in this study. These are also considered variants of the peptides. A peptide analogue as used herein, includes peptides that have amino acid molecules which mimic the structure of the natural amino acid e.g. an analog with a different backbone structure, or D-amino acid substitution. As a further example, although the amino acids used for synthesizing the peptides are in their L optical isomeric form, peptides with one or more of the amino acids in the sequence substituted with the D-form may have similar biological activities. The term "functional derivative" as used in the claims is meant to include fragments, variants, analogues or chemical derivatives of the peptide.

The use of the above-identified peptides in pharmaceutical formulations may be employed as possible treatment for disorders described herein, such as immunological disorders, cancer, fatigue, transplant rejection, and the like. The formulations may contain one of the identified peptides mixed with other active or inactive constituents, including other peptides. Alternatively, one of the listed peptides may be used to prepare the formulation together with peptides not listed here. They can be administered in the form of intravenous, intramuscular, intracutaneous, subcutaneous or intradermal. The mode of administration may also be intra-arterial injection that leads directly to the organ in need of treatment. Other modes of administration are transdermal, inhalation as powder or spray, and other forms of delivery known by one in the art. The formulation may also be orally taken, and may contain carriers that can be used to prevent gastric digestion of the peptide after oral intake or any other carriers known in the art.

The pharmaceutical formulation may include any of the known pharmaceutical carriers. Examples of suitable carriers include any of the standard pharmaceutically accepted carrier known to those skilled in the art. These include but are not limited to, physiological saline solution, water, emulsions including oil and water mixtures or triglyceride emulsions, and other types of agents, fillers, coated tablets and capsules. The appropriate carrier may be selected based on the mode of administration of the pharmaceutical composition.

In a further aspect of the present invention, enhanced derivatives of the peptide described herein and functional derivatives thereof are provided. The biologically active peptides of the present invention may be conjugated to other biologically effective or useful molecules to provide an additional effect or use or to enhance their therapeutic effectiveness. Many potential conjugating molecules, their biological effects and the methods for conjugation of the molecules to peptides are known in the art. Exemplary conjugating molecules include but are not limited to an organic compound, a carbohydrate, a sugar, a polysaccharide, an amino acid, an amino acid polymer, a peptide, a steroid, a protein, an isolated domain of a protein, a lipid molecule, a fatty acid, a bile acid, a polyamine, a protease inhibitor, and the like. A combination of conjugating molecules can also be used.

Some of the peptides of the invention have distinct therapeutic effects on a particular cell or tissue type. One important objective of conjugating molecules to peptide drugs is the targeting of the peptide to a particular location or compartment within the body of an individual being treated. In this way, the peptide drug and its effects can be concentrated at the location of the cell or tissue type on which it has the intended therapeutic effect. This can augment the effect that a similar molar amount of the free, unconjugated peptide would have. Other objectives of conjugating molecules can include, for example, extending the life of the peptide, altering the solubility of the peptide, altering the activity of the peptide, and altering the bioavailability of the peptide.

Chemical reactions for conjugating the instant peptides to the conjugating partners can be deduced by one skilled in the art without undue experimentation. Various conjugation techniques are described, for example, in Haas et al., Kidney Intl., 52(6):1693, 1997; Fiume et al., Ital J Gastroenterol Hepatol, 29(3):275, 1997; Di Stefano et al., Biochem. Pharmacol., 61(4):459, 2001; Huang et al., Chem. Biol., 7(7):453, 2000; Leopold et al., J. Pharmacokinet. Biopharm., 23(4):397, 1995; Patel et al., Bioconjugate Chem., 8(3):434, 1997; Kramer et al. J. Biol. Chem., 269(14): 10621, 1994; Toth et al. (J. Med. Chem., 42(19):4010, 1999; Kim et al., (Biomaterials, 23:2311, 2002; Oldham et al. (Int. J. Oncology, 16:125, 2000; and Fitzpatrick et al. Anticancer Drug Design, 10:1, 1995, all of which are incorporated by reference herein in their entireties.

Gene Therapy and Method of Treatment

Gene therapy based on the discovered peptide sequences can be performed by designing a nucleic acid sequence that code for one of these peptides. The nucleic acid may be synthesized chemically and operably ligated to a promoter, and cloned into an expression vector. The expression vector is then administered into the human body as the form of gene therapy for expression in the human cell. The term "genetic vectors" as used herein includes these expression vectors. Vectors that can be used for gene therapy includes adeno-associated virus (Mizuno, M. et al. (1998), Jpn J Cancer Res 89, 76-80), LNSX vectors (Miller, A. D. et al. (1993) Methods Enzymol 217, 581-599) and lentivirus (Goldman, M. J. et al. (1997) Hum Gene Ther 8, 2261-2268), the disclosures of which are incorporated herein by reference in their entireties.

Other vehicles for peptide delivery include expression vectors encoding the desired peptide that can be transferred into an organism which can replicate in the host organism to which it is desired to administer the peptide without significant detrimental effects on the health of the host organism. For example, the expression vectors may be transferred into an organism which is not pathogenic to the host organism to which it is desired to administer the peptide. In some embodiments the expression vector produces the desired peptide in a bacterial or fungal organism which does not have significant detrimental effects on the health of the host organism to which the peptide is to be administered. For example, the expression vector encoding the desired peptide may be an expression vector which produces the desired peptide in an organism such as lactic acid bacteria, *E. coli*, or yeast. In one embodiment, the expression vector produces the desired peptide in a microbe normally found in the mammalian gut or a microbe tolerated by the mammalian digestive tract. Some of the microbial species in which the desired peptide can be expressed include, but are not limited to, *Lactobacillus* species, such as *L. acidophilus, L. amylovorus, L. casei, L. crispatus, L. gallinarum, L. gasseri, L. johnsonii, L. paracasei, L. plantarum, L. reuteri, L. rhamnosus* or others; *Bifidobacterium* species, such as *B. adolescentis, B. animalus, B. bifidum, B. breve, B. infantis, B. lactis, B. longum* or others; *Enterococcus faecalis* or *Ent. facium*; *Sporolactobacillus inulinus*; *Bacillus subtilis* or *Bacillus cereus*; *Escherichia coli*; *Propionibacterium freudenreichii*; or *Saccharomyces cerevisiae* or *Saccharomyces boulardii*.

Nucleic acid sequences that encode the peptides of the present invention, chemically synthesized or produced by other means, including but not limited to the reverse transcription of mRNA to produce cDNA molecules, can be incorporated into expression vectors for gene transfer into the desired organisms by methods of genetic engineering familiar to those of skill in the art. The expression vectors may be DNA vectors or RNA vectors. For example, the expression vectors can be based on plasmid or viral genetic elements. The expression vectors can be vectors which replicate extrachromosomally or vectors which integrate into the chromosome.

The expression vectors comprise a promoter operably linked to a nucleic acid encoding a peptide of the present invention. The promoter may be a regulatable promoter, such as an inducible promoter, or a constitutive promoter. In some embodiments, the promoter may be selected to provide a desired level of peptide expression. In addition, if desired, the expression vectors may comprise other sequences to promote the production, presentation and/or secretion of peptides. In some embodiments a nucleic acid encoding a peptide of the present invention is operably linked to a nucleic acid sequence which directs the secretion of the peptide. For example, the nucleic acid encoding the peptide of the present invention may be operably linked to a nucleic acid encoding a signal peptide.

In some embodiments, the expression vectors which are engineered to encode the peptides of the present invention may be expression vectors which are adapted for expressing the peptide of the present invention in a bacterial species that makes up the normal gut flora of mammals, such as *Lactobacillus* species and *Bacillus subtilis* Examples of such expression vectors can be found in U.S. Pat. No. 6,100,388, to Casas, and U.S. Pat. No. 5,728,571, to Bellini, respectively. These documents are hereby expressly incorporated by reference in their entireties. It will be appreciated that any expression vector which facilitates the expression of a peptide of the present invention in an organism which is not detrimental to the health of the host organism to which the peptide is to be administered may be used.

In some embodiments, the expression vectors which are engineered to encode the peptides of the present invention may be expression vectors which are adapted for expressing the peptide of the present invention in a yeast species that is well tolerated by the mammalian gut, such as *Saccharomyces cerevisiae*; or, preferably, *Saccharomyces boulardii*, which can colonize the human gut and is used to treat certain forms of diarrhea. Yeast expression vectors can be used that constitutively express heterologous proteins and peptides, are highly stable, thus are well transmitted to progeny cells during mitosis and meiosis and may comprise coding sequence for a signal peptide or peptides that direct high levels of recombinant protein secretion. An example of such a yeast vector is given in U.S. Pat. No. 6,391,585, to Jang et al., which is hereby expressly incorporated by reference in its entirety.

The expression vectors encoding the peptides of the present invention may be introduced into the organism in which it is intended to express the peptides through techniques known in the art. These techniques include traditional methods of transforming bacteria, yeast, or other microbes, through the use of chemically competent bacterial cells, electroporation or lithium acetate transformation (for yeast), for example, as well as recent advances in the transformation of bacterial species recalcitrant to these procedures. In some embodiments, the expression vectors are introduced into lactic acid bacteria known to be recalcitrant to transformation using the method disclosed by Leer et al. (WO 95/35389), the disclosure of which is incorporated herein by reference in its entirety. The introduced sequences may be incorporated into microbial chromosomal DNA or may remain as extrachromosomal DNA elements.

This genetically engineered microbe containing the expression vector can then be inoculated into the alimentary canal, vagina, trachea, etc., to achieve sustained immunotherapy. In some embodiments, the organisms expressing the peptides of the present invention are ingested in an inactive form or, preferably, in live form. In the gut these microorganisms produce said peptides, release them into the lumen by secretion or by lysis of the microorganism or otherwise present the peptides to the host, whereby the peptides produce their intended effect upon the host organism. In other embodiments, peptides are presented to the host at the mucous membrane of the nasal passages, vagina or the small intestine.

Another method of the treatment is the use of liposomes as a means for delivering the specific nucleic acid to the cells in the human body. The nucleic acid (such as an expression vector containing a nucleic sequence that encodes peptides described herein can be delivered in an environment that encourages cellular uptake and chromosomal incorporation as described in Gao, X. and Huang, L. (1995) Gene Ther 2, 710-722 and U.S. Pat. No. 6,207,456, the disclosure of which is incorporated herein by reference in its entirety. Alternatively, the peptide itself can be encapsulated in the liposome and delivered directly, using a method described in U.S. Pat. No. 6,245,427, the disclosure of which is incorporated herein by reference in its entirety. All the scientific publications and patents indicated are incorporated herein by reference.

The nucleic acid sequences useful for the above-mentioned gene therapy and method of treatment include sequences that code for these peptides and functional derivatives thereof. Any one of the numerous nucleic acid sequences may be used to code for these peptides and their derivatives based on the degenerate codon system.

EXAMPLE 1

The Effects of CMS-001 and CMS-008 on Exercise-Induced Fatigue of Mice

Objective:
To investigate the anti-fatigue effects of CMS-001 and CMS-008 on BALB/c mice.

Methods:
BALB/c mice exhaustive swimming model was used to observe the anti-fatigue effects of CMS-001 and CMS-008. The exhaustive swimming time, liver glycogen, serum urea nitrogen (BUN), and blood lactic acid level was observed after the administration of CMS-001 and CMS-008. The serum malondialdehyde (MDA), superoxide dismutase (SOD), alanine aminotransferase (ALT), and aspartate aminotransferase (AST) levels were also observed to investigate the possible anti-fatigue mechanism of CMS-001 and CMS-008.

Results:
CMS-001 and CMS-008 at suitable concentrations, were found to be able to lengthen the exhaustive swimming time of mice, reduce the BUN level, increase the liver glycogen level, and decrease the accumulation of blood lactic acid, with statistical significance compared with the saline control (P<0.05). It was also found that CMS-001 and CMS-008 were also able to decrease the elevation of blood MDA, ALT, and AST levels and increase the activity of SOD during exhaustive exercise, with statistical significance compared with the saline control (P<0.05).

Conclusion:
CMS-001 and CMS-008 were found to have anti-fatigue properties and may be used in the management of fatigue related disorders.

1 Material and Methods 1.1 Drug and Reagents

CMS-001 and CMS-008 were custom synthesized by Shenzhen Kangzhe Pharmaceutical Co. Ltd., Shenzhen, PR China.

Urea Nitrogen reagent kit: Beckman Coulter, Inc., Fullerton, Calif., USA.

Anthracene Ketone reagent kit: Shanghai Fifth Union Laboratory, Shanghai, China, PRC.

MDA and SOD reagent kits: Nanjing Jiancheng Bio-engineering Corporation, Nanjing, China, PRC.

AST and ALT reagent kits: Beijing Zhongsheng Bio-engineering High Technology Corporation, Beijing, PRC.

1.2 Animals

Male BALB/c mice, specific pathogen free (SPF) grade, weighing 18-22 g were obtained from Academy of Military Medicines and Sciences Experimental Animal Center, PR China.

The mice were randomized into groups of CMS-001 (20 μg/kg/day, 5 μg/kg/day), CMS-008 (500 μg/kg/day, 125 μg/kg/day), and saline control. The test substance was administered by intraperitoneal injection once per day for 30 continuous days. A week after the start the of the test substance administration, the mice were trained to swim for 10 min, at water temperature of 25±1° C.

1.3 Experimental Equipment

Swimming tank (50 cm×50 cm×40 cm).
Fully automated Biochemistry Analyser RA-1000.
Lactic acid automated analyser 1500SPORT.

1.4 The Effect of CMS-001 and CMS-008 on the Exhaustive Swimming Time of Mice[1]

30 min after the last injection, the mice were weighed, and lead pieces corresponding to 5% of the body weight were wrapped to the tails of the mice at about 1 cm away from the body. The mice were placed in the swimming tank, at water depth of 30 cm and temperature of 25±1° C. The limbs of the mice were kept moving in the whole process. The time of swimming until the death was recorded.

1.5 The Effect of CMS-001 and CMS-008 on Serum Urea Nitrogen Level after Exercise 30 min after the last injection, the mice were placed to swim in the swimming tank without addition of weight for 90 min, at water depth of 30 cm temperature of 30±1° C. The mice were then allowed to rest for 30 min, and blood was collected from the orbital sinus. The serum was isolated and the BUN was determined by a fully automated Biochemistry Analyser.

1.6 The Effect of CMS-001 and CMS-008 on Liver Glycogen Level of Mice[2]

30 min after the last injection, the mice were killed by cervical dislocation and the liver was dissected, washed with saline, and blotted dry with filter paper. About 100 mg liver was accurately weighed and the liver glycogen level was determined by the Anthracene Ketone reagent kit.

Glycogen weight (mg) in every 100 g of liver=DU/DS× 0.5× homogenization liquid vol./liver weight (g)×100×0.9.

Whereas:
DU=absorbency of sample
DS=absorbency of standard
Homogenization liquid vol=8 ml

1.7 The Effect of CMS-001 and CMS-008 on Blood Lactic Acid Level of Mice after Exercise[3]

30 min after the last injection, 20 μl of blood was first collected from the orbital sinus. The mice were then weighed, and lead pieces corresponding to 4% of the body weight were wrapped to the tails of the mice at about 1 cm away from the body. The mice were placed to swim in the swimming tank for 10 min, at water depth of 30 cm and temperature of 30±1° C. The limbs of the mice were kept moving in the whole process. Immediately after the exercise and after resting for 20 min, 20 μl of blood was collected from the orbital sinus again. The blood was added into 40 μl hypotonic buffer and sonicated. Lactic acid level in the blood was determined by the lactic acid analyzer.

The amount of lactic acid increase after exercise is calculated based on the amount of lactic acid level immediately after exercise minus the lactic acid level before exercise.

The amount of lactic acid elimination after rest was calculated based on the amount of lactic acid level immediately after exercise minus the lactic acid level after rest.

1.8 The Effect of CMS-001 and CMS-008 on the Serum SOD, MDA, AST, and ALT Levels after Exhaustive Exercise 30 min after the last injection, the mice were placed to swim in the swimming tank without addition of weight at water depth of 30 cm and temperature of 25±1° C.[4]. By the first time the mice sunk, the mice were rescued and blood was collected from the orbital sinus immediately. The serum was isolated and the MDA, SOD, AST, and ALT levels determined.

1.9 Statistical Method

Difference between groups were analyzed by ANOV Analysis of variance.

2 Results

TABLE 1.1

The effect of CMS-001 and CMS-008 on the exhaustive swimming time of mice

| groups | Dosages (μg/kg/day) | No. | Swimming time (min) | Swimming-time extension (%) |
|---|---|---|---|---|
| CMS-001 | 20 | 15 | 99.8 ± 30.6* | 48.0* |
| CMS-001 | 5 | 18 | 105.7 ± 19.8* | 56.7* |
| CMS-008 | 500 | 15 | 116.5 ± 17.7* | 72.7* |
| CMS-008 | 125 | 18 | 106.5 ± 19.4* | 57.9* |
| Saline | — | 16 | 67.5 ± 28.0 | |

*compared with the saline control, P < 0.05

TABLE 1.2

The effect of CMS-001 and CMS-008 on serum urea nitrogen level after exercise

| groups | Dosages (μg/kg/day) | No. | Urea Nitrogen (mmol/l) |
|---|---|---|---|
| CMS-001 | 20 | 17 | 7.3 ± 2.1* |
| CMS-001 | 5 | 18 | 6.9 ± 1.6* |
| CMS-008 | 500 | 17 | 7.1 ± 2.0* |
| CMS-008 | 125 | 18 | 7.2 ± 2.3* |
| Saline | — | 17 | 9.0 ± 2.5 |

*compared with the saline control, P < 0.05

TABLE 1.3

The effect of CMS-001 and CMS-008 on liver glycogen level of mice

| groups | Dosages (μg/kg/day) | No. | liver glycogen (mg/100 g liver tissue) |
|---|---|---|---|
| CMS-001 | 20 | 8 | 1567 ± 604* |
| CMS-001 | 5 | 10 | 439 ± 271* |
| CMS-008 | 500 | 8 | 1408 ± 457* |
| CMS-008 | 125 | 10 | 1275 ± 726* |
| Saline | — | 10 | 271 ± 217 |

*compared with the saline control, P < 0.05

TABLE 1.4

The effect of CMS-001 and CMS-008 on blood lactic acid level of mice after exercise

| groups | Dosages (μg/kg/day) | No. | Lactic acid increase after exercise (mmol/l) | Lactic acid elimination after rest (mmol/l) |
|---|---|---|---|---|
| CMS-001 | 20 | 15 | 2.56 ± 0.41* | 3.14 ± 0.64* |
| CMS-001 | 5 | 13 | 2.60 ± 0.33* | 2.96 ± 0.33* |
| CMS-008 | 500 | 15 | 2.23 ± 0.30* | 3.71 ± 0.22* |
| CMS-008 | 125 | 13 | 2.70 ± 0.15* | 3.62 ± 0.57* |
| Saline | — | 14 | 4.60 ± 0.16 | 2.00 ± 0.44 |

*compared with the saline group P < 0.05

TABLE 1.5

The effect of CMS-001 and CMS-008 on the serum SOD, MDA, AST, and ALT levels after exhaustive exercise

| groups | Dosages (μg/kg/day) | No. | MDA (nmol/l) | SOD (U/ml) | AST (U/L) | ALT (U/L) |
|---|---|---|---|---|---|---|
| CMS-001 | 20 | 9 | 4.4 ± 0.2* | 400.6 ± 45.6* | 117.0 ± 19.2* | 32.7 ± 3.0* |
| CMS-008 | 500 | 9 | 4.1 ± 0.4* | 415.7 ± 31.5* | 116.6 ± 18.8* | 32.9 ± 5.2* |
| Saline | — | 9 | 6.9 ± 0.3 | 342.7 ± 27.3 | 145.2 ± 32.3 | 40.2 ± 8.2 |

*compared with the saline group P < 0.05

Conclusion

This study showed that CMS-001 and CMS-008 have the following properties:

1. Extend the swimming time of the mice, showing that CMS-001 and CMS-008 can increase the exercise capacity of the animal[5].
2. Decrease the BUN of the mice, showing that CMS-001 and CMS-008 can decrease the necessity for catabolism of protein for energy production during exercise[6].
3. Increase liver glycogen reserve of the animal during rest, giving the animals increased capacity for exercise[6].
4. Decrease the blood lactic acid level after exercise, and increase the speed of lactic acid elimination thereafter, showing that CMS-001 and CMS-008 can decrease the speed of lactic acid production or lactic acid elimination during exercise[7].
5. Decrease the MDA level, showing that CMS-001 and CMS-008 can decrease free radical production during exercise[8].
6. Increase the SOD level, showing that CMS-001 and CMS-008 can increase free radical elimination during exercise[8].
7. Decrease ALT and AST level, showing that CMS-001 and CMS-008 can protect heart and liver cellular damage during exercise.
8. CMS-001 and CMS-008 may be useful in the management of exercise related fatigue disorders.

References

The following references are incorporated herein by reference in their entireties.
1. Mizunoya W, Oyaizu S, Ishihara K, et al. Protocol for measuring the endurance capacity of mice in an adjustable-current swimming pool. Biosci Biotechnol Biochem. 2002 May; 66(5):1133-6.
2. H E Ling, WANG Ming, CHEN Run etc. The effect of blood lactic acid blood serum carbamide nitrogen and liver hepatin affected by gen-seng. Prevent Medicine Literature Information, 2002, 8(3):293-294.
3. WANF Xiao-xue, QIU Juan, SONG Yu etc. Study on Effect of Theanine of Fatigue. China Commonality Sanitation Journal, 2002, 18(3):315-317.
4. Thomas D P, Marshall K I. Effects of repeated exhaustive exercise on myocardial subcellular membrane structure. Int J Sport Med, 1988, (9):257-260.
5. JIN Zong-lian. Evaluation principle and method of function food. Beijing: Beijing University Publishing Company, 1995.
6. Sanitation ministry, Evaluation progress and test methods of health care food. Ministry of Public Health, PR China.
7. Westerblad, et al. Changes of intracellular pH due to repetitive stimulation of single fibers from mouse skeletal muscle. J Physiol; 1992 April; (499):49-71.
8. Groussard C, Rannou-Bekono F, Machefer G, et al. Changes in blood lipid peroxidation markers and antioxidants after a single sprint anaerobic exercise. Eur J Appl Physiol. 2003 March; 89(1):14-20.

EXAMPLE 2

Immuno-Regulatory Effects of CMS-001 on Radiotherapy Induced Immuno-Comprised Mice Objective:

To observe the immuno-regulatory effects of CMS-001 on radiotherapy induced immuno-compromised animal model.

Methods:

An immuno-compromised mice model was first set up by $Cs^{137}$ irradiation. CMS-001 was then applied and the change in T lymphocyte proliferation rate was then analyzed by the MTT method.

Results:

At 20 μg/kg/day, CMS-001 was found to be able to increase the rate of T lymphocyte proliferation, with statistical significance (P<0.05).

1 Material and Methods 1.1 Drug and Reagents

CMS-001: Custom synthesized by Shenzhen Kangzhe Pharmaceutical Co. Ltd., Shenzhen, PR China.

Hank's solution, Bovine fetal serum, and RPMI-1640: Hyclone, Logan, Utah.

ConA and MTT: Sigma Chemical Co., St. Louis, Mo., USA.

1.2 Experimental Animals

Male Balb/c mice, specific pathogen free grade (SPF), weighing 18-22 g were obtained from Academy of Military Medicines and Sciences experimental animal center, PR China.

1.3 Preparation of Animal Model, Administration of CMS-001, and Quantitation of T Lymphocyte Proliferation Rate[1]

Balb/c male mice were randomized into groups of: CMS-001 (20 μg/kg/day, 5 μg/kg/day), the saline control, and the normal control. All mice except the normal control group were exposed to 600 rad $Cs^{137}$ (82.83 rad/min for 7.2 min). The test substance was dissolved in 0.5 ml saline, and applied intraperitoneally once per day for 15 continuous days after irradiation. On the day after the last test substance administration, the spleens of the mice were dissected aseptically. The spleens were dispersed to single cells, washed, and the cell concentration adjusted to $4 \times 10^6$/ml with RPMI-1640. To a 96 wells culture plate, 100 μl cells and 100 μl Con A (to final concentration of 5 μg/ml) were added per well. Baseline blank controls without ConA were also prepared. The cells were incubated at 37° C. and 5% $CO_2$ for 68 hrs. The proliferation of T lymphocyte was determined by the MTT method [2]. The stimulation index was calculated according to the following: Stimulate index (SI)=mean OD value of ConA wells/mean OD value of the baseline blank wells.

2 Result

TABLE 2.1

The effect of CMS-001 on T lymphocyte proliferation in radiation induced immuno-comprised mice.

| Groups | dosage | No. | SI |
|---|---|---|---|
| CMS-001 | 20 μg/kg/day | 10 | 1.27 ± 0.19* |
| saline control | — | 8 | 1.11 ± 0.08 |
| normal control | — | 10 | 3.42 ± 0.93* |

*compared with saline group P < 0.05

3 Conclusion

CMS-001 was found to be able to stimulate the T lymphocyte proliferation in radiation induced immuno-compromised mice, with statistical significance, showing that CMS-001 may be used as an immuno-stimulant on immuno-comprised patients after radiotherapy.

References

The following references are incorporated herein by reference in their entireties.
1. New drugs (Western medicine) research direction principle before clinic. Chinese Sanitation Ministry Drug Political Situation. 1993, 7:128-137.
2. Qiu Zhi-qiang. The influence of Fuzheng buxuegao to blood system and immunity function affected by radiotherapy. Lanzhou Medical Transaction, 2003, 3(28).

EXAMPLE 3

Effect of CMS-014 on the Survival of Skin Allograft in Mice

Objective:
To investigate the immunosuppressive effect of CMS-014 by the skin allograft model.
Methods:
Pieces of tail skin from $C_{57}BL/6$ mice were transplanted to BALB/c mice and the mean survival time (MST) of the skin allograft was observed.
Results:
CMS-014 was found to be able to prolong the survival of the skin allograft, with statistical significance (p<0.05) compared with the saline control.
Conclusion:
CMS-014 may be used as an immuno-suppressing agent to control the rejection reaction after organ transplantation.

1 Materials 1.1 Drugs and Other Reagents

CMS-014: Custom synthesized by Shenzhen Kangzhe Pharmaceutical Co. Ltd., Shenzhen, PR China.

Cyclosporine A (CsA): Novartis Pharmaceutical Co. Ltd., Basel, Switzerland.
Saline: China OTSUKA Pharmaceutical Co. Ltd., Tianjin, PR China.
$Na_2S$: Tianjin Beilian Chemical Co. Ltd., Tianjin, PR China.

1.2 Animals

Recipients: Balb/c($H-2^d$) mice, specific pathogen free grade (SPF), 6 weeks old, weighing 18-22 g: Military Medical Academy of Science, China.
Donors: $C_{57}BL/6(H-2^b)$ mice, SPF, 6 weeks old, weighing 18-22 g: Military Medical Academy of Science, China.

2 Grouping and Treatment 2.1 Grouping and Test Substance Administration

Balb/c mice were randomized into groups of CMS-014 (500 μg/kg/day, 250 μg/kg/day, 125 μg/kg/day), Cyclosporine A (10 mg/kg/day), and saline control (0.5 ml/day). Half of the mice were male and half were female.
The test substances were dissolved in 0.5 ml saline and intraperitoneally injected for 5 days before the skin transplantation, followed by daily injection until the end point of rejection of the skin graft.

2.2 Skin Grafting

A patch of hair at the back of Balb/c mice was removed by 8% $Na_2S$ solution. On the next day, a wound bed of approximately 1 $cm^2$ was produced by removing the skin surgically, and then a piece of full-thickness tail skin of 1 $cm^2$ from sex-matched donor $C_{57}BL/6J$ mice was placed onto the wound bed. The surgical site was covered and protected with a layer of paraffin gauze, and a covering plaster was applied. The plaster was removed 6 days after transplantation[1], and the recipient mice were monitored daily for the viability of the allograft. The end point of rejection was taken as only less than 10% of the allograft remained viable[2].

2.3 Statistical Analysis

Statistical analysis was performed with Kaplan-Meier survival test.

3 Results

TABLE 3.1

Effect of CMS-014 on the MST of mice skin allografts

| Groups | Dosages | No. | MST (days) |
|---|---|---|---|
| CMS-014 | 500 μg/kg/day | 9 | 9.8 ± 0.4* |
| CMS-014 | 250 μg/kg/day | 10 | 9.8 ± 0.5* |
| CMS-014 | 125 μg/kg/day | 9 | 10.0 ± 0.5* |
| CsA | 10 mg/kg/day | 9 | 11.6 ± 0.8* |
| saline | 0.5 ml/day | 8 | 8.1 ± 0.4 |

*Compared with saline control group, p < 0.05

4 Conclusion

CMS-014 was found to be able to prolong the survival of the skin allograft, with statistical significance (p<0.05) compared with the saline control. CMS-014 may be used as an immuno-suppressing agent to control the rejection reaction after organ transplantation.

5 References

The following references are incorporated herein by reference in their entireties.

[1] Ming Jiankuo, Wang Xingbing, Huang Baojun, et al. Peptide Nucleic Acid Antisense Prolongs Skin Allograft Survival by Means of Blockade of CXCR3 Expression Directing T Cells into Graft. The Journal of Immunology, 2003, 170:1556-1565.

[2] Steven H. Borenstein, Jeremy Graham, et al. CD8+ T Cells Are Necessary for Recognition of Allelic, But Not Locus-Mismatched or Xeno-, HLA Class I Transplantation Antigens. The Journal of Immunology, 2000; 165:2341-2353.

EXAMPLE 4

The Inhibition Effect of CMS-017 and CMS-023 on Hepatitis B Virus in Vitro

EXAMPLE 4a

Human Hepatitis

Test peptides were added to the culture medium of 2.2.15 cell line. After incubation, the concentrations of hepatitis B surface antigen (HBsAg), hepatitis B e antigen (HBeAg), and hepatitis B virus DNA (HBV-DNA) in the culture medium were determined and compared with that of the control. Peptides CMS-017 and CMS-023 at suitable concentration were found to have anti-hepatitis B virus activity in vitro, with statistical significance compared with the control (P<0.05). It is concluded that these peptides may be used in the management of hepatitis B virus infection.

1 Materials

The peptides cms-017 and cms-023 were custom synthesized (of 1-amino acids origin) by American Peptide Company, Inc., Sunnyvale, Calif., USA.

2.2.2.15 cell strain, transfected by human hepatitis B virus (HBV) DNA, was supplied by the National Center For Drug Screening (Shanghai, China) (test one) and the Department Of Infectious Diseases Of The First Hospital affiliated to Beijing University (test two).

Cell culture medium MEM was from GIBCO®, Invitrogen, Carlsbad, Calif., USA.

Elisa kits for HBsAg and HBeAg assays were from Shanghai Shiye Kehua Biotech. Company, Shanghai, PR China.

Fluorescence quantitative PCR kit for the determination of HBV-DNA was from DA-AN gene company of Zhongshan Medical University, Guangzhou, PR China.

2 Methods

Test 1

Inhibitory Effect of Peptides on HBsAg and HBeAg at Maximum Non-Toxic Concentration 2.2.15 cells at log phase were harvested and adjusted to $2\times10^6$/ml with MEM (containing 10% fetal bovine serum, 100 mg/ml penicillin, and 100 U/ml streptomycin). The suspension was inoculated on a 24-well culture plate with 1.5 ml per well, and incubated at 37° C., 5% $CO_2$ for 48 hours for attachment. The peptides were added to the final concentration of 400 μg/ml with 3 parallel wells per sample. One set of blank control (3 wells) was also prepared, in which the peptide was replaced with culture medium. The plate was incubated at 37° C. for 4 days, the culture medium was then exchanged with freshly prepared medium (of the same composition as the original), and the plate was incubated for a further 4 days. By the end of incubation, the supernatants of the culture were collected, and the titers of HBsAg and HBeAg were determined by ELISA method according to the instruction of the detection kit manufacturer. The inhibition percentages of the drugs were calculated as below:

% inhibition=(Average concentration of control−Average concentration of sample)/Average concentration of control×100%

Test 2

Inhibitory Effect of Peptides on HBV-DNA

The preparation and incubation of cell suspension was repeated as in test 1 above, but at the peptide concentration of 160 μg/ml. By the end of incubation, the supernatants were collected and the HBV-DNA concentrations were determination by fluorescence quantitative PCR, according to the instruction of the detection kit manufacturer.

% inhibition=(Average DNA concentration of control−Average DNA concentration of sample)/Average DNA concentration of control×100%

Statistics

Student t test was used for the statistical analysis. P<0.05 was taken as statistically significant.

Results

TABLE 4.1

Inhibitory effect of peptides on HBsAg and HBeAg at 400 μg/ml

| Peptide | Inhibition ratio to HBsAg | Inhibition ratio to HBeAg |
| --- | --- | --- |
| CMS-017 | 68.6%* | 62.2%* |
| CMS-023 | 58.4%* | 53.7%* |

*Compared with the blank control, P < 0.05

TABLE 4.2

Inhibitory effect of peptides on HBV-DNA at 160 μg/ml

| Peptide | % HBV-DNA inhibition |
| --- | --- |
| CMS-017 | 90.8%* |
| CMS-023 | 70.8%* |

*Compared with the blank control, P < 0.05.

Conclusion

At suitable concentration, CMS-017 and CMS-023 were found to be able to inhibit the development of hepatitis B virus in vitro, with statistical significance compared with the control (P<0.05). This shows that CMS-017 and CMS-023 may be used in the management of hepatitis B related viral infections.

EXAMPLE 4b

The Antiviral Effects of CMS-017 on Duck Hepatitis B In Vivo

Objective:

To investigate the antiviral effects of CMS-017 on duck hepatitis B virus (DHBV) in vivo.

Methods

CMS-017 dissolved in saline was applied to Chongqing duck hepatitis B animal model by intramuscular injection for 28 days. The serum levels of DHBV DNA and DHBsAg (duck hepatitis B surface antigen) were observed by serum dot-blot hybridization and ELISA respectively and compared with blank control.

Results

CMS-017 was found to be able to reduce the serum levels of DHBV DNA and DHBsAg during the treatment period (P<0.01). Upon discontinuation of treatment for 7 days, rebound was not observed.

Materials and Methods

1 Animal Model[2]

0.1 ml DHBV DNA positive serum ($5 \times 10^7$ copies/ml) was inoculated into the abdominal cavity of one-day old Chongqing ducks to set up the hepatitis animal model. 10 days after inoculation, blood samples were collected from the external jugular vein and success of infection was confirmed by dot-blot hybridization with DHBV DNA probe labeled with digoxi[3]. The ducks were bred to 2 weeks old for entrance into the study.

2 Grouping and Administration

Ducks confirmed with DHBV infection were randomly divided into the following groups:

1) Control group (n=12): Normal saline. 1 ml per day, once per day, and applied by intramuscular injection.

2) CMS-017 group (n=12): 200 μg/kg/day CMS-017 (dissolved in 1 ml normal saline) applied by intramuscular injection, once per day.

The treatment lasted for 4 weeks, and observation continued for another one week after termination of treatment. 1 ml blood samples were drawn from the external jugular vein on days 0, 7, 14, 21, 28, and 35 from the start of treatment. The sera were isolated[4] and stored at −20° C. until analysis.

3 Parameters to be Monitored

1) DHBV DNA Serum Level

DHBV DNA probe was fluorescent-labeled according to the labeling kit protocol from the manufacturer (Roche Co.). Duck sera were dot-blotted (2 dot per sample) onto nitrocellulose membrane and hybridized with fluorescent-labeled probe for DHBV DNA quantitation[3]. DHBV DNA 40 μl+DHBsAg 100 μl was used as internal standard. CDP-Star fluorimetry reagent was used for amplification of the fluorescence. Vuego Scan (Brisa-620st) scanner was used for film scanning, and Discovery Series Quantity One software for quantitative analysis of the blots. The blot value was described as "volume" (volume=intensity×mm$^2$)

2) DHBsAg Serum Level

DHBsAg level was determined by ELISA method[5-8], and the O.D value was obtained by ELISA reader (Bio-TEK Co.) at 490 nm 4 Statistical Analysis Paired t-test was carried out for each group using SPSS software.

Results

1. The changes of the serum DHBV DNA concentration

TABLE 4.3

Serum DHBV DNA titer during pre- and post-treatment

| | Pre-treatment | Week 1 | Week 2 | Week 3 | Week 4 | Week 5 |
|---|---|---|---|---|---|---|
| | | | DHBV DNA (volume) | | | |
| Normal saline | 2055.9 ± 521.8 | 1952.5 ± 621.5 | 2048.6 ± 692.3 | 2031.2 ± 722.3 | 1886.0 ± 641.3 | 2118.5 ± 468.1 |
| CMS-017 | 2207.0 ± 237.5 | 1991.8 ± 378.9* | 1925.0 ± 549.9* | 1743.9 ± 555.0* | 1544.9 ± 389.7* | 1742.7 ± 437.0* |

*Compared with saline control P < 0.05

2. The changes of the serum DHBsAg level

TABLE 4.4

Serum DHBsAg O.D. value during pre- and post-treatment

| | Pre-treatment | Week 1 | Week 2 | Week 3 | Week 4 | Week 5 |
|---|---|---|---|---|---|---|
| Normal saline | 0.949 ± 0.688 | 0.761 ± 0.540 | 0.892 ± 0.762 | 0.867 ± 0.802 | 0.701 ± 0.673 | 0.871 ± 0.634 |
| CMS-017 | 0.928 ± 0.402 | 0.761 ± 0.328 | 0.668 ± 0.310* | 0.551 ± 0.268* | 0.479 ± 0.279* | 0.488 ± 0.182* |

*Compared with saline control P < 0.05

Conclusion

At suitable concentration, CMS-017 was found to have anti-hepatitis properties in vivo, with statistical significance compared with the saline control (P<0.05). CMS-017 may be used in the management of viral infection related disorders.

References

The following references are incorporated herein by reference in their entireties.

1. Chen Yaxi, Guo shuhua, Zhang Dingfeng, et al. Foundation and application of Chongqing duck hepatitis B model. Chinese Journal of Hepatology. 1993; 1(2):89-91.
2. Chen Yaxi, Guo shuhua, Chen Xuehua. Preparation and application of DHBV DNA probe labeled with digoxin. Journal of Chongqing University of Medical Sciences. 1994; 19(4):295-297.
3. Tang Ni, Huang Ailong, Guo shuhua, et al. Systemic foundation and application of serological parameters of humoral immunity to duck hepatitis B virus. Chinese Journal of Hepatology. 2001; 9(1):13-15.

4. Tang Ni, Huang Ailong, Guo shuhua, et al. Purification of Duck hepatitis B surface antigen and its applications. Journal of Chongqing University of Medical Sciences. 2001; 26(1):14-16.
5. Tang Ni, Huang Ailong, Guo shuhua, et al. A comparison of specifically immune response in DHBV-infected ducks. Chinese Journal of Hepatology. 2001; 9(3):166-168.
6. Tang Ni, Huang Ailong, Qi Zhenyuan, et al Immune response of acutely infected ducks to duck hepatitis B virus. Chinese Journal of Microbiology and Immunology 2000; 2(4):24-29.
7. Chen Yaxi, Guo shuhua, Qi Zhenyuan, et al. An experimental study of lamivudine against duck hepatitis B virus in combination with famciclovir. Chinese Journal of Hepatology. 2001; 9(4):209-211.
8. Qiu Zhi-qiang. The influence of Fuzheng buxuegao to blood system and immunity function affected by radiotherapy. Lanzhou Medical Transaction, 2003, 3 (28).

EXAMPLE 5

The Inhibitory Effect of Cms024-16 on Nude Mice-Transplanted Human Gastric Carcinoma BGC-823 Xenograft 1 Materials 1.1 Drugs and Reagents CMS024-16: Custom synthesized by Shenzhen Kangzhe Pharmaceutical Co. Ltd., Shenzhen, PR China.
5-Fu: Tianjin Jinyao Amino Acid Co., Tianjin, PR China.
Fetal bovine serum (FBS): Hyclone, Logan, Utah.
RPMI-1640 cell culture medium: GIBCO®, Invitrogen, Carlsbad, Calif., USA.

1.2 Animals

Healthy female BALB/c (nu/nu) nude mice, specific pathogen free grade (SPF), 4-5 weeks old: Academy of Military Medical Sciences, China.

1.3 Cell Lines

Human gastric carcinoma cell line BGC-823: Cancer Research Department, China Medical Science Institute.

2 Methods 2.1 Animal Model Preparation and Determination of Anti-Tumor Effects[1]

Hunan gastric carcinoma cell line BGC-823 at log phase were adjusted to the concentration of $2 \times 10^7$/ml and then inoculated subcutaneously to the back of nude mice (0.1 ml per mouse). The inoculated animals were randomized into groups of CMS024-16 (160 μg/kg/day, 320 μg/kg/day, and 640 μg/kg/day, all at 0.2 ml/day), positive control (5-Fu, 20 mg/kg/day at 0.2 ml/day), and negative control (normal saline, 0.2 ml/day). Administration of test substances by intraperitoneal injection was started on the next day after tumor implantation once per day for 30 continuous days. On the next day after the last injection, the tumor masses were collected and their weights determined Inhibition rate=(Mean weight of negative control−Mean weight of test group)/(Mean weight of negative control)×100%

2.2 Statistical Analysis

Data were expressed as Mean±SD. ANOVA of the SPSS software was used for the statistical analysis. P values<0.05 were taken as statistically significant.

3. Results

TABLE 5.1

The inhibition effect of CMS024-16 on nude mice-transplanted human gastric carcinoma BGC-823 xenograft

| Group | Dosage | N | Tumor weight (g) | Inhibition rate (%) |
|---|---|---|---|---|
| CMS024-16 | 640 μg/Kg/day | 8 | 1.31 ± 0.77* | 54.4* |
| CMS024-16 | 320 μg/Kg/day | 8 | 1.59 ± 1.017* | 44.7* |
| CMS024-16 | 160 μg/Kg/day | 8 | 1.32 ± 0.68* | 54.0* |
| 5-Fu | 20 mg/Kg/day | 9 | 1.70 ± 0.70* | 40.8* |
| Normal saline | 0.2 ml/day | 8 | 2.87 ± 1.05 | — |

*Compared with normal saline group, p < 0.05.

4. Conclusion

CMS024-16 at a dosage of 160-640 μg/kg/day, was found to be able to inhibit the growth of nude mice-transplanted human gastric carcinoma BGC-823 xenograft, with statistical significance compared with the normal saline group (P<0.05).

Reference

The following reference is incorporated herein by reference in its entirety.
1. Li X H, Zhang G Y, Luo F J, Xu M H, Li Q. The effect of *Helicobacter pylori* on the expression of metallo proteinases in gastric carcinoma cell lines. World J Chinese Digestion, 2003, 11(5):544-546.

EXAMPLE 6

The Inhibitory Effects of Peptides on Hepatocarcinoma H22 In Vivo

Objective:
To investigate the effects of peptides on the growth of hepatocarcinoma H22 in mice.
Methods:
BALB/C mice were randomized into groups of saline control, 5-Fu, normal control, peptides. Liver carcinoma H22 cells were transplanted by intraperitoneal injection and the test substances administered also by intraperitoneal injection once daily. The survival time of the mice was recorded and compared with the controls.
Results:
At doses of 80 μg/kg/day, CMS-024.04, CMS-024.05, CMS-024.14, CMS-024.16 were found to be able to prolong the survival of mice transplanted with H22 tumor cells, with statistical significance compared with the saline control group (P<0.05).
Conclusions:
CMS-024.04, CMS-024.05, CMS-024.14, and CMS-024.16 were found to be able to prolong the survival of mice with transplanted liver cancer H22, showing that these peptides may be used for the management of cancers.

1 Materials and Methods

1.1 Drugs and Reagents

CMS-024.04, CMS-024.05, CMS-024.14, and CMS-024.16 were custom manufactured by Shenzhen Kangzhe Pharmaceutical Co. Ltd., Shenzhen, PR China.

5-FU (5-fluorouracil) was from Tianjin Jinyao Aminophenol Ltd., Tianjin, China.

Saline was from China OTSUKA Pharmaceutical Co. Ltd., Tianjin, China.

RPMI-1640 and Fetal bovine serum (FBS) were from GIBCO®, Invitrogen, Carlsbad, Calif., USA.

D-Hanks' solution were from Sigma Chemical Co., St. Louis, Mo., USA.

1.2 Animals

Healthy BALB/c mice (CLA grade, 6-8 weeks, weight 18-22 g) were from the Animal Center of Military Medical Academy of Science, Beijing, China.

1.3 Cell Lines

Mice hosting hepatic carcinoma H22 cell strain were from Tumor Department of Medical Institute of China Medical Academy of Science, Beijing, China.

1.4 Grouping of Animals

Healthy BALB/c mice were randomized into groups of CMS-024.04, CMS-025.05, CMS-024.14, and CMS-024.16 (80 µg/kg/day), 5-Fu (20 mg/kg/day, once for every two days), saline (0.2 ml/day), and normal group (without tumor cell inoculation).

1.5 Administration of Hepatic Carcinoma H22 Mice Model

Mice inoculated with hepatocarcinomas for 6-8 days were sacrificed. The ascites was collected and the cell concentration adjusted to $5 \times 10^7$/ml with D-Hanks' solution. 0.2 ml of this was inoculated intraperitoneally to each BALB/c mouse except for the normal controls.

1.6 Test Substance Administration

Administration of test substance was started on the next day after the tumor cell inoculation. The peptides and saline were applied daily and 5-FU once every two days for 60 continuous days or until the death of the mice.

1.7 Survival Time Recording

The time of death was recorded and survival time prolongation calculated. Survival time prolongation was calculated as below:

Survival prolongation (%)=(Average survival days of test group)−(Average survival days of saline control group)/(Average survival days of saline group)×100%.

The mice that survived for more than 60 days were considered as long-term survivors.

1.8 Statistical Method

Kaplan-Meier method was used for statistical comparison and P values equal to or less than 0.05 was taken as statistically significant.

2 Results

The experiment was done in two separate times, with results as below.

TABLE 6.1

Effect of peptides on the survival of mice transplanted with H22 hepatocarcinoma

| Groups | Dosage | N | Survival time (days) | Survival time (days) | Survival Prolongation (%) |
|---|---|---|---|---|---|
| CMS-024.04 | 80 µg/kg | 16 | 19.0 ± 0.9 | 20.2 ± 4.4* | 15.8* |
| CMS-024.05 | 80 µg/kg | 16 | 19.0 ± 1.0 | 19.3 ± 2.4* | 10.4* |
| Saline control | 0.2 ml/day | 16 | 18.0 ± 0.3 | 17.4 ± 2.1 | — |
| 5-Fu | 20 mg/kg | 16 | 30.0 ± 2.0 | 32.5 ± 6.3* | 84.5* |
| Normal | — | 16 | 60 | 60 | — |

*Compared to saline control group, P < 0.05

TABLE 6.2

Effect of peptides on the survival of mice transplanted with H22 hepatocarcinoma

| Groups | Dosage | N | Survival time (days) | Survival time (days) | Survival Prolongation (%) |
|---|---|---|---|---|---|
| CMS-024.14 | 80 µg/kg | 16 | 16.0 ± 0.0 | 27.6 ± 8.5* | 50.3 |
| CMS-024.16 | 80 µg/kg | 16 | 18.0 ± 1.0 | 29.0 ± 7.9* | 57.8 |
| Saline control | — | 16 | 16.0 ± 0.1 | 18.4 ± 3.3 | — |
| 5-Fu | 20 mg/kg | 16 | 18.0 ± 0.4 | 24.5 ± 11.1* | 33.3 |
| Normal | — | 16 | 60 | 60 | — |

*Compared to saline control group, P < 0.05

3 Conclusions

CMS-024.04, CMS-024.05, CMS-024.14, and CMS-024.16 were found to be able to prolong the survival of mice with transplanted liver cancer H22, with statistical significance compared with the saline control group, showing that these peptides may be used for the management of cancers.

References

The following references are incorporated herein by reference in their entireties.

[1] Y Zhai and Z J Lu. Effect of thalidomide on tumor growth in mouse hepatoma H22 model. Ai Zheng, December 2003; 22(12):1301-6.

[2] Y X Yang, L Zhu, X He, et al. Antitumor activity of mitoxantrone-nanosphere against murine liver tumor H22. Sichuan Da Xue Xue Bao Yi Xue Ban, January 2004; 35(1):68-70.

EXAMPLE 7

Effects of CMS-030 on Carrageenin Induced Foot Swelling in Rats

Objective:

To investigate the anti-inflammatory properties of CMS-030.

Methods:

Carrageenin induced foot swelling animal model was used to study the anti-inflammatory properties of CMS-030.

Results:

At the dosage of 2-20 μg/ml, CMS-030 was found to be able to suppress the foot swelling in the treatment group compared to the control groups, with statistical significance (P<0.01).

Conclusion:

CMS-030 was shown to have a statistically significant anti-inflammatory effect on carrageenin induced foot swelling rat animal model.

1 Materials and Methods 1.1 Drugs and Reagents

CMS-030: Custom synthesized by Shenzhen Kangzhe Pharmaceutical Co. Ltd., Shenzhen, PR China.

Carrageenin: Sigma Chemical Co., St. Louis, Mo., USA.

Dexamethasone (DXM): Tianjin JinYao Co. Ltd., Tianjin, PR China.

1.2 Animals

Wistar rats, 6-8 weeks old, weighing 180-220 g, Vitalriver Experiment Animal Co. Ltd., Beijing, PR China.

1.3 Methods[1]

Wistar rats were divided randomly into DXM group (0.2 mg/kg/day), saline control group (1 ml/day), and three dosages of CMS-030 groups (2, 10, 20 μg/ml/day). All of the drugs were diluted to 0.5 ml with saline, and were administered intraperitoneally (i.p) daily. Two weeks after drug administration, 0.15 ml of 1% carrageenin saline solution was applied to the right foot by subcutaneous injection. 0.5 hr later, the circumference of right foot was measured precisely, and foot swelling was calculated by subtracting the pre-challenge circumference from the post-challenge value Inhibition index (%)=(foot swelling of saline control group−foot swelling of drug group)/foot swelling of saline control group× 100%.

1.4 Statistical Analysis

Statistical analysis was performed with analysis of One-Way ANOVA.

2 Results

TABLE 7.1

Anti-inflammatory action of CMS-030 on carrageenin induced foot swelling in rats

| Group | Dose | n | Pre-challenge circumference (cm) | Swelling (cm) 0.5 hr | Inhibition Index (%) 0.5 hr |
|---|---|---|---|---|---|
| CMS-030 | 2 μg/kg/d | 10 | 2.78 ± 0.06 | 3.20 ± 0.87** | 37.0** |
| CMS-030 | 10 μg/kg/d | 10 | 2.76 ± 0.03 | 3.10 ± 0.10** | 50.2** |
| CMS-030 | 20 μg/kg/d | 10 | 2.74 ± 0.04 | 3.12 ± 0.05** | 43.8** |
| DXM | 0.2 mg/kg/d | 9 | 2.49 ± 0.05 | 2.74 ± 0.10** | 63.0** |
| Saline | 0.5 ml/d | 10 | 2.80 ± 0.06 | 3.47 ± 0.08 | — |

**compared with the saline control group, P < 0.01.

Conclusion

Carrageenin induced foot swelling in rats was an established animal model of acute inflammation in vivo, and was used to evaluate the anti-inflammatory effects of drugs[2]. Carrageenin can induce over-synthesis of prostaglandin in the inflammation site. Together with other vasoactive substances, the over-produced prostaglandin will induce local swelling. CMS-030 was found to be able to inhibit the foot swelling induced by carrageenin in rats, with statistical significance (P<0.01). CMS-030 has therefore been shown to have anti-inflammatory properties.

References

The following references are incorporated herein by reference in their entireties.

[1] Li Jinhua, Zhang Huiqing, Zheng Kezhi, et al Inhibitory effects of Orgotein on the swelling of hind paw in rats induced by carrageenin. Suzhou University Journal of Medical Science, 2002, Vol, 22(4):386-388.

[2] Huang Zhili, Kagoshima Masatoyo, Kagawa Eiichiro, Anti-inflammatory and ulcerogenic effects of 3-(N,N-diethylamino) propylindometacin HCl. Acta Pharmacologica Sinica, 1997, Vol, 18(4):306-308.

EXAMPLE 8

Effect of CMS-030 on Obesity

Objective:

To determine anti-obesity effect of CMS-030 using overfeed rat as the animal model.

Methods:

An obesity model was developed by feeding rats with a high nutrition diet for 6 weeks. The rats were then treated with CMS-030 (subcutaneous, at dosages of 150, 300, and 600 μg/kg/day), or with saline for 4 weeks. The rats were weighed once per week, and were killed for the measurement of abdominal and testicular fat pads and blood lipid at the end of the experiment.

Results:

CMS-030 was found to be able to decrease the body weight, fat pad indexes, serum triglyceride level, and total serum cholesterol level in rats, with statistical significance compared with the saline control group (P<0.05).

Conclusion:

CMS-030 has anti-obesity properties, and may be used in the management of diet induced obesity disorders.

Materials and Methods

1 Materials 1.1 Test substance and Animal

CMS-030 was custom synthesized by Shenzhen Kangzhe Pharmaceutical Co. Ltd., Shenzhen, PR China.

Sprague-Dawley (SD) rats, specific pathogen free grade, weighing 135±15 g, male: The Experimental Animal Center of First Military Medical University.

1.2 Reagent kits

Triglyceride kit: Shanghai Rongcheng Biotechnology Laboratory.

Total serum cholesterol kit: Zhongsheng Beikong Biotechnology Holding Ltd.

2 Methods

The prescriptions of high and normal nutrition feed were prepared in compliance with The Guideline for Pre-clinical Research of Anti-obesity Drug, issued by State Food and Drug Administration, PR China (SFDA)[1].

The obesity model[2] was set up by feeding rats with a high nutrition diet for 6 weeks. Rats served with normal diet were used as normal control. The obese rats were then treated with CMS-030 (150, 300, and 600 µg/kg/day, once daily, subcutaneous) or saline for 4 weeks. All rats were on normal diet during test substance treatment. The rats were weighed weekly and killed at the end of the experiment for the measurement of abdominal and testicular fat pads, and the weights of spleen, liver, kidney, and thymus. The rat blood was also drawn for analysis of blood lipids.

Index of fat pad was calculated as: fat pad weight (g)/body weight (g)×1000.

Index of organ was calculated as: organ weight (g)/body weight (g)×1000.

3 Statistical Analysis

The data are presented as mean±standard deviation. A paired t test or single-factor ANOVA was applied in comparison within each group or between groups using the software DAS (Drug And Statistics Ver1.0). P<0.05 was taken as statistically significant.

4 Results

TABLE 8.1

Effect of CMS-030 on body weight of rats (unit: gram)

| Group | n | 0 week | 1 week | 2 week | 3 week | 4 week |
|---|---|---|---|---|---|---|
| Normal control | 10 | 224.6 ± 15.6* | 252.0 ± 18.0* | 277.9 ± 20.2* | 305.0 ± 26.9* | 332.0 ± 22.7* |
| Saline control | 10 | 342.6 ± 23.8 | 386.2 ± 26.9 | 386.1 ± 24.6 | 410.8 ± 25.7 | 408.8 ± 24.5 |
| CMS-030: 600 µg/kg/day | 12 | 339.0 ± 27.0 | 365.4 ± 25.7 | 355.1 ± 24.6* | 361.7 ± 32.6* | 369.9 ± 30.0* |
| CMS-030: 300 µg/kg/day | 12 | 338.0 ± 22.8 | 369.7 ± 26.1 | 359.6 ± 23.7* | 364.3 ± 22.6* | 366.3 ± 24.5* |
| CMS-030: 150 µg/kg/day | 12 | 327.0 ± 26.9 | 348.9 ± 23.9* | 346.5 ± 22.7* | 351.8 ± 25.0* | 354.0 ± 26.3* |

Compared with saline control: *p < 0.05

TABLE 8.2

Effect of CMS-030 on fat pad index of rat

| Group | n | Index of body fat pad | Index of testicular fat pad |
|---|---|---|---|
| Normal control | 10 | 4.3 ± 1.2* | 4.6 ± 0.9* |
| Saline control | 10 | 6.0 ± 1.8 | 5.5 ± 0.9 |
| CMS-030: 600 µg/kg/day | 12 | 4.5 ± 1.1* | 5.0 ± 0.7* |
| CMS-030: 300 µg/kg/day | 12 | 3.8 ± 2.1* | 4.0 ± 1.1* |
| CMS-030: 150 µg/kg/day | 12 | 3.9 ± 1.6* | 3.6 ± 0.9* |

Compared with saline control: *p < 0.05

TABLE 8.3

Effect of CMS-030 on blood triglyceride (TG) and total cholesterol (TCH) of rats

| Group | n | TG (mg/dL) | TCH (mg/dL) |
|---|---|---|---|
| Saline control | 8 | 101.8 ± 31.2 | 333.3 ± 24.5 |
| Normal control | 8 | 36.4 ± 9.1* | 225.7 ± 55.0* |
| CMS-030: 600 µg/kg/day | 12 | 40.6 ± 7.9* | 228.1 ± 39.8* |
| CMS-030: 300 µg/kg/day | 11 | 32.7 ± 6.7* | 234.9 ± 39.1* |
| CMS-030: 150 µg/kg/day | 12 | 51.5 ± 19.4* | 270.9 ± 33.0* |

Compared with saline control: *p < 0.05

TABLE 8.4

Effect of CMS-030 on food intake by rats (unit: g/day)

| Group | Week one | Week two | Week three | Week four |
|---|---|---|---|---|
| Normal control | 13.2 ± 1.3* | 18.3 ± 6.1* | 18.6 ± 0.35 | 17.6 ± 2.7 |
| Saline control | 11.7 ± 2.3 | 15.5 ± 3.0 | 18.21 ± 0.43 | 18.4 ± 0.59 |
| CMS-030: 600 µg/kg/day | 13.8 ± 5.4 | 15.9 ± 1.7 | 18.2 ± 0.69 | 18.5 ± 0.61 |
| CMS-030: 300 µg/kg/day | 13.2 ± 4.8 | 16.9 ± 1.6 | 18.1 ± 0.74 | 18.4 ± 0.59 |
| CMS-030: 150 µg/kg/day | 13.2 ± 3.1 | 16.1 ± 1.8 | 18.3 ± 0.67 | 17.8 ± 0.53* |

Compared with saline control: *p < 0.05

TABLE 8.5

Effect of CMS-030 on organs indexes of rats

| Group | n | Thymus index | Liver index | Spleen index |
|---|---|---|---|---|
| Saline control | 12 | 1.1 ± 0.3 | 25.5 ± 2.3 | 2.0 ± 0.3 |
| Normal control | 8 | 1.3 ± 0.3 | 25.5 ± 1.2 | 2.4 ± 0.2* |
| CMS-030: 600 µg/kg/day | 12 | 1.1 ± 0.2 | 24.3 ± 2.2 | 2.0 ± 0.2 |
| CMS-030: 300 µg/kg/day | 12 | 1.0 ± 0.3 | 23.1 ± 1.3* | 2.0 ± 0.2 |
| CMS-030: 150 µg/kg/day | 12 | 0.9 ± 0.2 | 25.9 ± 3.6 | 2.0 ± 0.2 |

Compared with saline control: *p < 0.05

Conclusion

CMS-030, at a suitable dosage, was found to be able to induce weight loss and reduce blood lipid levels in a nutritionally obese rat, with statistical significance compared with saline control (P<0.05). Appetite was not significantly affected during the administration of the substance. CMS-030 may be useful in the management of nutrition related obesity and hyperlipidemia.

References

The following references are incorporated herein by reference in their entireties.
1. SFDA, PR China. The guideline for pre-clinical research of new drugs. 1993.193-194.
2. Bays H E. Current and investigational anti-obesity agents and obesity therapeutic treatment targets. Obes Res. 2004; 12 (8):1197-1211.

EXAMPLE 9

Effects of CMS-030 on Delayed Hypersensitivity in Mice

Objective:
To investigate the inhibitory effect of CMS-030 on delayed hypersensitivity (DTH) in mice.
Methods:
2,4-dinitrofluorobenzene (DNFB) induced ear swelling was used to demonstrate the immunosuppressive effects of CMS-030.
Results:
At 10 µg/kg/day, CMS-030 was found to be able to suppress DNFB-induced ear swelling in mice, with statistical significance compared with the saline control ($P<0.01$).
Conclusion:
CMS-030 has immunosuppressive properties and may be useful for the management of immunity related disorders.

1 Materials and Methods

1.1 Drugs and reagents

CMS-030: Custom synthesized by Shenzhen Kangzhe Pharmaceutical Co. Ltd., Shenzhen, PR China.
2,4-dinitrofluorobenzene (DNFB): Smack Co. Ltd.
Sodium sulfide ($Na_2S$): Tianjin Beilian Chemical Co. Ltd., Tianjin, PR China.

1.2 Animals

Balb/c mice, specific pathogen free (SPF) grade, 6-8 weeks old, weighing 18-22 g: Military Medical Academy of Science, PR China.

1.3 Methods

BALB/c mice were randomized into groups of saline control (0.5 ml/day) and CMS-030 (10 µg/kg/day). The test substance was dissolved in 0.5 ml saline, and was administrated intraperitoneally once per day for two weeks before sensitization.
The mice were depilated with 8% $Na_2S$ solution at the abdomen one day before the sensitization. DNFB was dissolved in acetone/olive oil (4:1) to final concentration of 1% and 50 µl was applied to the depilated area for sensitization. Four days after the initial sensitization, 10 µl of the 1% DNFB solution was applied topically to the right ear to elicit delayed hypersensitivity inflammation. The same volume of solvent without DNFB was applied to the left ear as the baseline. 24 hrs later, a 6 mm diameter punch was used to collect a piece of ear tissue from the same location of the left and right ear, and the tissue was weighed accurately. The ear swelling was calculated by subtracting the weight of tissue from the right ear with that of the left ear from the same mouse[1] Inhibit rate (%)=(Ear swelling of saline control−Ear swelling of test group)/Ear swelling of saline control×100%.

1.4 Statistical Analysis

Statistical analysis was performed with One-Way ANOVA by SPSS.

2 Results

TABLE 9.1

The inhibitory effects of CMS-030 on DH in mice

| Group | Dosage | n | Ear swelling (mg) | Inhibit rate (%) |
|---|---|---|---|---|
| CMS-030 | 10 µg/kg/day | 17 | 3.69 ± 2.31* | 46.5* |
| Saline | 0.5 ml/day | 18 | 6.91 ± 2.50 | — |

*Compared with saline control group, $p < 0.01$

3 Conclusion

CMS-030 was found to be able to inhibit the delayed hypersensitivity response of mice to DNFB, with statistical significance compared with the saline control ($P<0.05$). This showed that CMS-030 may be used for the management of hypersensitivity related immunity disorders.

Reference

The following reference is incorporated herein by reference in its entirety.
[1] Li Weidong, Ren LianSheng, Lin Zhibin, et al. Preliminary study on immunomodulating actions of Actarit in mice. Journal of Beijing Medical University, 2000, Vol, 1(32): 1-3.

EXAMPLE 10

Studies on the Immuno-Suppressive Properties of CMS-030 In Vivo

Objective:
To investigate the anti-allograft-rejection properties of CMS-030 and the possible mechanisms of action.
Methods:
The immuno-suppressive properties of CMS-030 was observed with the T-lymphocyte proliferation test and Mixed lymphocyte reaction (MLR) in vitro. The effect of CMS-030 on the survival of allograft was observed on mice skin and cardiac muscle allograft animal model in vivo. The effect of CMS-030 on the transformed T-cell and spleen cell IL-2 secretion of the allograft recipient was also observed.
Conclusion:
CMS-030 was observed to have anti-allograft-rejection properties. This may be mediated via suppression of T-lymphocyte activities and IL-2 secretion by lymphocytes.

1 Materials and Methods

1.1 Animals

Five week old specific pathogen-free female and male Balb/c ($H-2^b$) and $C_{57}BL/6J$ ($H-2^d$) mice: The Institute for Laboratory Animals of Military Medical Academy of Science (Beijing, China). Half male and half female.
C57BL/6 new born mice were from self-breeding.

1.2 Drugs and Other Reagents

CMS-030: Custom synthesized by Shenzhen Kangzhe Pharmaceutical Co. Ltd., Shenzhen, PR China.

Cyclosporine (CsA): Novartis Pharmaceutical Co. Ltd., Basel, Switzerland. Dissolve to 0.5 ml final volume for all CsA groups.

Bovine serum, RPMI-1640, Hank's solution: GIBCO®, Invitrogen, Carlsbad, Calif., USA.

MTT, ConA: Sigma Chemical Co., St. Louis, Mo., USA.

NaS: Tianjin Beilian Fine Chemicals Co., Ltd., Tianjin, PR China.

Mouse IL-2 Elisa kit: R&D Systems Inc., Minneapolis, Minn., USA.

1.3 Grouping of Animals

For the in vivo tests, the mice were randomized into groups of
CMS-030 (10 μg/kg/day).
CMS-030 (2 μg/kg/day).
CsA (10 mg/kg/day).
Normal saline (0.5 ml/day).

The solutions were applied by intraperitoneal injection, once per day for 5 days before transplantation and continued for another 20 days after the surgery.

1.4 Effect of CMS-030 on T-Lymphocyte Proliferation In Vitro[1]

Healthy Balb/c mice spleens were dissected aseptically and immersed in ice-cold D-Hank's solution. Spleen cells were prepared by disrupting the spleen with frosted glass slides in RPMI-1640. The cells were washed twice in RPMI-1640 at 4° C. and 1,200 rpm for 10 min. The cells were then counted and adjusted to the concentration required for each assay. Cell viability in the experiment was determined by trypan blue exclusion and should be greater than 95%.

The spleen cells from healthy mice were cultured in 96-well plates, adjusted to a concentration of $4\times10^5$ per well. CMS-030 was added to the wells of final concentration of 40 μg/ml, 8 μg/ml, 1.6 μg/ml, and 0.32 μg/ml. The plates were incubated in a humidified atmosphere at 37° C., 5% $CO_2$ for 68 hr in the presence of concanavalin A (ConA) at a final concentration of 5 μg/ml. In the positive control group, no CMS-030 was added. In the negative control group, neither ConA nor CMS-030 was added. The proliferation of lymphocytes was measured by the 3-[4,5-dimethylthiazol-2-yl]-2,5-diphenyltetrazolium bromide (MTT) colorimetric assay at the end of incubation. 20 μl of MTT was added to each well, and the plates were further incubated for 4 hr. Then, 100 μl of 0.04 M HCl in isopropyl alcohol was added to each well in order to solubilize the formazan precipitate. The OD of each sample was measured spectrophotometrically at 570 nm referenced at 630 nm

1.5 Effect of CMS-030 on Mixed Lymphocyte Reaction (MLR) In Vitro[2]

Healthy Balb/c mice spleen cells were washed with ice-cold D-Hank's solution and resuspended in RPMI-1640 to $8\times10^6$/well to form the responder cells. Spleen cells suspension from healthy $C_{57}BL/6J$ mice were incubated with mitomycin (25 μg/ml) for 45 minutes in RPMI 1640 at 37° C. and in 5% $CO_2$, then washed with RPMI-1640 and resuspended to $8\times10^6$/well to form the stimulant cells. Using a 96 wells culture plate, to the test groups, add in 100 μg responder cells and 100 μg stimulant cells, and 20 μl CMS-030 to final concentrations of 40 μg/ml, 8 μg/ml, 1.6 μg/ml, or 0.32 μg/ml. To the positive control group, 100 μl of responder cells, 100 μl stimulant cells, and 20 μl RPMI-1640 were added. To the negative control group, 200 μl stimulant cells and 20 μl RPMI-1640 were added. Six parallel wells were used for each combination. After 5 days of incubation at 37° C. and 5% $CO_2$, the proliferation of lymphocytes was measured by the MTT colorimetric assay.

1.6 The Effect of CMS-030 on the Survival of Heart Transplant In Vivo[3]

The donor hearts were dissected from 24 hour old newborn $C_{57}BL/6J$ mice. The hearts were immersed in D-Hank's solution and the blood from the cardiac cavity was cleared. The hearts were transplanted subcutaneously in the ear pinnae passages of healthy adult Balb/c recipients. The air in the heart and the passage was expelled by slight pressure. Starting from the sixth day after transplantation, the electrocardiogram (ECG) of the transplanted heart was taken daily. Absence of ECG signal for 3 consecutive days showed that the transplantation surgery was unsuccessful and the mice were excluded from the statistics analysis. The ECG was followed daily and time to rejection was taken as the day on which the ECG signal disappeared. Test substances were administered intraperitoneally starting from 6 days before surgery. There were 10 mice per group. Cyclosporine A was administered at 10 mg/kg/day, CMS-030 at 10 μg/kg/day or 2 μg/kg/day, and saline at 0.5 ml/kg/day. Statistical analyses were performed using Kaplan Meier log-rank test comparisons with saline-treated group.

1.7 Effect of CMS-030 on the Survival of Skin Allograft In Vivo[4]

A patch of hair at the back of Balb/c mice was removed by 8% $Na_2S$ solution. On the next day, a wound bed of approximately 1 $cm^2$ was produced by removing the skin surgically, and then a piece of full-thickness tail skin of 1 $cm^2$ from sex-matched donor $C_{57}BL/6J$ mice was placed onto the wound bed. The surgical site was covered and protected with a layer of paraffin gauze, and a covering plaster was applied. The plaster was removed 8 days after transplantation, and the recipient mice were monitored daily for the viability of the allograft. The end point of rejection was taken as only less than 10% of the allograft remained viable. Intraperitoneal treatment with test substances was started 6 days before surgery. There were 10 mice per group. Cyclosporine A was administered at 10 mg/kg/day, CMS-030 at 10 μg/kg/day or 2 μg/kg/day, and saline at 0.5 ml/kg/day. The treatment was continued for another 20 days after surgery.

1.8 Effect of CMS-030 on T Lymphocyte Proliferation In Vivo[5]

Spleen cells from the skin graft recipient mice were isolated and re-suspended in RPMI-1640 to $4\times10^6$/ml. 100 μl/well cells were added into a 96-well plate. To the test wells, 100 μl ConA was added to the final concentration of 5 μg/ml. To the control wells, 100 μl RPMI-1640 was added instead. Four parallel wells per condition. The cells were incubated for 68 hrs at 37° C. and 5% $CO_2$. The proliferation of lymphocytes was measured by MTT colorimetric assay. The OD of each sample was measured spectrophotometrically at 570 nm referenced at 630 nm. The data were expressed as the stimulation index, which was the OD of the test group divided by the OD of the control group.

1.9 Effect of CMS-030 on IL-2 Levels In Vivo[6]

Spleen cells from the skin graft recipient mice were isolated and re-suspended in RPMI-1640 to $2 \times 10^6$/ml. 1.5 ml/well cells were added into a 24 wells plate and incubated for 24 hrs for attachment. 100 µl ConA was added to the final concentration of 10 µg/ml. The cells were incubated for another 48 hrs and the supernatant subsequently collected after centrifugation. IL-2 levels in culture supernatants were determined by ELISA.

1.10 Statistical Analysis

A Kaplan Meier log-rank test comparison with control group was used for allograft survival time analysis. Comparison of means with variances by 2-tailed Student t test was used for other experiments.

2 Results

TABLE 10.1

Effect of CMS-030 on T-lymphocyte proliferation in vitro

| Group | Dose of drugs | No. | OD |
|---|---|---|---|
| CMS-030 | 40 µg/ml | 6 | 0.332 ± 0.062* |
| CMS-030 | 8 µg/ml | 6 | 0.281 ± 0.041* |
| CMS-030 | 1.6 µg/ml | 6 | 0.311 ± 0.027* |
| CMS-030 | 0.32 µg/ml | 6 | 0.315 ± 0.043* |
| Positive control | — | 6 | 0.421 ± 0.055 |
| Negative control | — | 6 | 0.109 ± 0.003* |

*Compared with saline control group, $p < 0.01$

TABLE 10.2

Effect of CMS-030 on Mixed lymphocyte reaction (MLR) in vitro

| Group | Dose of drugs | No. | OD |
|---|---|---|---|
| CMS-030 | 40 µg/ml | 6 | 0.192 ± 0.019* |
| CMS-030 | 8 µg/ml | 6 | 0.285 ± 0.004* |
| CMS-030 | 1.6 µg/ml | 6 | 0.361 ± 0.036* |
| Positive control | — | 6 | 0.440 ± 0.043 |
| Negative control | — | 6 | 0.145 ± 0.019 |

*Compared with saline control group, $p < 0.01$

TABLE 10.3

The effect of CMS-030 on the survival of heart transplant in vivo

| Group | Dose of drugs | No. | Mean survival time (day) |
|---|---|---|---|
| CMS-030 | 10 µg/kg/d | 9 | 12.0 ± 2.2* |
| CMS-030 | 2 µg/kg/d | 9 | 11.5 ± 1.9* |
| CsA | 10 mg/kg/d | 8 | 13.8 ± 1.3* |
| Saline | 0.5 ml/d | 10 | 9.1 ± 1.4 |

*Compared with saline control group, $p < 0.05$

TABLE 10.4

Effect of CMS-030 on the survival of skin allograft in vivo

| Group | Dose of drugs | No. | Mean survival time (day) |
|---|---|---|---|
| CMS-030 | 10 µg/kg/d | 9 | 14.1 ± 1.2* |
| CMS-030 | 2 µg/kg/d | 10 | 13.4 ± 1.5* |
| CsA | 10 mg/kg/d | 9 | 15.0 ± 1.4* |
| Saline | 0.5 ml/d | 9 | 11.0 ± 1.3 |

*Compared with saline control group, $p < 0.01$

TABLE 10.5

Effect of CMS-030 on T lymphocyte proliferation in vivo

| Group | Dose of drugs | No. | Stimulation index |
|---|---|---|---|
| CMS-030 | 10 µg/kg/d | 9 | 1.6 ± 0.3* |
| CMS-030 | 2 µg/kg/d | 10 | 1.9 ± 0.5* |
| CsA | 10 mg/kg/d | 9 | 1.8 ± 0.3* |
| Saline | 0.5 ml/d | 9 | 2.3 ± 0.5 |

*Compared with saline control group, $p < 0.01$

TABLE 10.6

Effect of CMS-030 on IL-2 levels in vivo

| Group | Dose of drugs | No. | IL-2 (pg/ml) |
|---|---|---|---|
| CMS-030 | 10 µg/kg/d | 9 | 599.0 ± 121.8* |
| CMS-030 | 2 µg/kg/d | 10 | 577.4 ± 163.1* |
| CsA | 10 mg/kg/d | 9 | 595.2 ± 162.8* |
| Saline | 0.5 ml/d | 9 | 787.4 ± 227.8 |

*Compared with saline control group, $p < 0.01$

Conclusion

At the concentration of 0.32 µg/ml to 40 µg/ml, CMS-030 was found to be able to statistically significantly inhibit ConA induced T lymphocytes proliferation in vitro, showing that CMS-030 can inhibit the proliferation of T lymphocytes in vitro. MLR is an experiment in vitro to determine the response of lymphocytes to different HLA-II molecules, and is a model for the prediction of rejection potential after organ transplantation[7]. At the concentration of 1.6 µg/ml to 40 µg/ml, CMS-030 was found to be able to statistically significantly inhibit mixed lymphocyte reaction, indicating that CMS-030 can decrease the rejection potential after organ transplantation.

The heart transplant and skin allograft experiments were animal models for the study of the suppression of rejection after transplant[7]. CMS-030 at dosage of 2 µg/kg/day and 10 µg/kg/day was found to be able to prolong the survival of the transplant, with statistical significance, showing that CMS-030 can suppress rejection of the transplant by the host immune response. Analysis of the spleen cells isolated from the skin graft recipient mice showed that CMS-030 was able to suppress the activation of the lymphocyte and the secretion of IL-2 by the T lymphocytes, both with statistical significance, showing that the prolongation of survival of the allograft was achieved by suppression of the immune response of the recipient animal.

References

The following references are incorporated herein by reference in their entireties.

[1] Roma Kalra, Shashi P. Singh, Juan C, et al Immunosuppressive and Anti-Inflammatory Effects of Nicotine Administered by Patch in an Animal Model. Clinical and Diagnostic Laborarory Immunology, May 2004, 563-568.
[2] Dubey D P, Yunis I, Yunis E J, et al. Cellar typing: mixed lymphocyte response and cell mediated lympholysis. American Society for Microbiology, 1986, 847-848.
[3] Vakeva A Laurila P, Meri S, et al. Regulation of complement membrane attack complex formation in myocardial infarction. Am J Pathol, 1993, 143:65.
[4] Ming Jiankuo, Wang Xingbing, Huang Baojun, et al. Peptide Nucleic Acid Antisense Prolongs Skin Allograft Survival by Means of Blockade of CXCR3 Expression Directing T Cells into Graft. The Journal of Immunology, 2003, 170:1556-65.
[5] Maria A. Puertollano, Manuel A. de Pablo, et al. Relevance of Dietary Lipids as Modulators of Immune Functions in Cells Infected with *Listeria monocytogenes*. Clinical and Diagnostic Laboratory Immunology. 2002, 9:352-357.
[6] Mayumi H, Himeno K, Shin T, et al. Drug-induced tolerance to allografts in mice. Immunobiology, 1985, 169(2): 147-161.
[7] Rene J. Duquesnoy Li Y P. Transplantation immunobiology. 2002, 10:5-7.

EXAMPLE 11

The Effect of Peptides on Exercise-Induced Fatigue of Mice

Objective:
To investigate the anti-fatigue effects of peptides on Balb/c mice.
Methods:
Male Balb/c mice swimming time was used as the animal model for studying the anti-fatigue effect of peptides.
Results:
CMS-001.30 and CMS-001.31 was found to be able to lengthen the swimming time of mice, with statistical significance compared with the control (P<0.01).
Conclusion:
CMS001-30 and CMS001-31 has anti-fatigue properties and may be used on the management of fatigue related disorders.

1 Material and Methods

1.1 Drug and Reagents

CMS-001.30 and CMS-001.31 were custom synthesized by Shenzhen Kangzhe Pharmaceutical Co. Ltd., Shenzhen, PR China.

Erythropoietin (EPO): Japan Kunpeng Medical Corporation.

1.2 Animals

Balb/c mice, male, specific pathogen free (SPF) grade, weighing 18-22 g: Academy of Military Medicines and Sciences Experimental Animal Center, PR China.

1.3 Groupings and Method[1]

Balb/c male mice were randomized into groups of CMS-001.30 (20 µg/kg/day), CMS-001.31 (20 µg/kg/day), EPO (1000 u/kg/day, three times per week), and saline control. The test substance was dissolved in 0.5 ml saline and applied intraperitoneally once per day for 30 continuous days (EPO was replaced with saline if EPO was not applied). On the tenth day, the mice were trained to swim for 10 min at water temperature of 25±1° C. 30 min after the last test substance administration, the mice were placed to swim in the swimming tank (50 cm×50 cm×40 cm). The depth of water was 30 cm and water temperature 25±1° C. The limbs of the mice were kept moving in the whole process. The swimming (min) time of the mice until death was recorded.

Exhaustive swimming time extension rate (ESTR) (%)= (Mean exhaustive swimming time of test group−Mean exhaustive swimming time of saline control)/(Mean exhaustive swimming time of saline control)×100%.

1.4 Statistics

Difference between groups were analyzed by ANOVA Analysis of variance

2 Results

TABLE 11.1

The effect of peptides on the exhaustive swimming time of mice

| Groups | Dosages | No. | Swimming time (min) | ESTR (%) |
|---|---|---|---|---|
| CMS-001.30 | 20 µg/kg/day | 20 | 186.4 ± 15.2* | 88.3* |
| CMS-001.31 | 20 µg/kg/day | 20 | 174.3 ± 29.2* | 76.0* |
| EPO | 1000 u/kg/day, 3 times per week | 20 | 126.1 ± 20.4* | 31.3* |
| Saline | 0.5 ml/day | 20 | 99.0 ± 11.2 | — |

*compared with the saline group P < 0.01

3 Conclusion

CMS001-30 and CMS001-31 were found to have anti-fatigue properties and can be used for the management of fatigue related disorders.

Reference

The following reference is incorporated herein by reference in its entirety.
1. Mizunoya W, Oyaizu S, Ishihara K, et al. Protocol for measuring the endurance capacity of mice in an adjustable-current swimming pool. Biosci Biotechnol Biochem. 2002 May; 66(5):1133-1136.

Based on the above information, various pharmaceutical formulation can be made from the disclosed peptides. The pharmaceutical formulation may include any of the known pharmaceutical carriers. Examples of suitable carriers include any of the standard pharmaceutically accepted carrier known to those skilled in the art. These include but are not limited to, physiological saline solution, water, emulsions including oil and water mixtures or triglyceride emulsions, and other types of agents, fillers, coated tablets and capsules. The appropriate carrier may be selected based on the mode of administration of the pharmaceutical composition.

The pharmaceutical formulation can be administered via intravenous injection, intramuscular injection, intraperitoneal injection, subcutaneous injection, and subcutaneous implantation. The peptide may also be administered in any form of oral administration such as, for example, a tablet, capsule, suspension, solution, and the like, in the usual form without modification or in slow release form, or with or without gastro-enteric protection. The peptide can also be applied in any form of topic application such as an ointment, cream, gel, etc., with or without a transdermal facilitating device. The peptide may also be interpreted into its genetic sequence and cloned into an expression system, on its own or in combination with other peptide sequences, to generate a resulting peptide molecule to make use of the activity of the peptide as described herein.

The dose of each peptide may be 1 ng-10 g per kg body weight. A preferred dose is 10 ng-10 mg per kg, and more preferably 1 μg-1 mg per kg for an injection mode of administration. However, the effective dose can be as low as 1 ng per kg body weight, since one or more of the peptides may operate through receptors that will induce a cascade of normal physiological responses. Alternatively, one or more of the peptides can just be an initiator for a whole cascade of reaction. For an oral intake, the amount may be 1 ng-10 g per day per kg body weight, more preferably 0.1 μg-1 g per day per kg body weight and even more preferably 1 μg-10 mg per day.

Gene therapy based on the above peptide sequences may be performed based on methods known in the art, and also based on patent publication WO 03/006492A2, which is incorporated by reference in its entirety herein. The peptides may also be conjugated to other enhancer molecules based on the teaching disclosed in patent publication WO2004/055042A1 and which is incorporated by reference in its entirety herein.

References

The following references are incorporated herein by reference in their entireties.
1. Principles of Pre-clinical Research of New Drugs, People's Republic of China. 1993, 7:134-135.
2. Shuyun Xu, Rulian Bian, Xiu Chen. Methodology of pharmacological experiment. People's Health Publishing House. 1991, 1221-1234.
3. Principle of new drug research in pre-clinic issued by Ministry of Health, People's Republic of China. 1993, 7:140.
4. Jinsheng He, Ruizhu Li, Tingyi Zong. The study on MTT reduction method of testing NK cell activity. China Immunology Journal. 1996, 1(6):356-358.
5. Qian Wang. Modern medical experiment method. People's Health Publishing House. 1998, 482-483.
6. Principle of new drug research in pre-clinic issued by Ministry of Health, People's Republic of China. 1993, 7:141.
7. Principle of new drug research in pre-clinic issued by Ministry of Health, People's Republic of China. 1993, 7:132-133.
8. Principle of new drug research in pre-clinic issued by Ministry of Health, People's Republic of China. 1993, 7:128-129.
9. Yuanpei Zhang, Huaide Su. Phamalogical experiment (second edition). People's Health Publishing House. 1998, 137-138.
10. Jiatai Li, clinical pharmacology (second edition). People's Health Publishing House. 1998, 1338-1339.

EXAMPLE 12

Delivery of Peptides Through Genetically Engineered *Lactobacillus* Bacterial Species The following is provided as one exemplary method to deliver peptides of this invention to a host as described above. A DNA sequence that encodes one of the peptides listed in table A above is synthesized by chemical means and this DNA sequence is inserted into an expression vector using standard techniques of genetic engineering familiar to those skilled in the art. The expression vector selected contains a constitutive promoter functional in Lactobacilli, a multiple cloning site for the introduction of DNA sequences in a specific 5' to 3' orientation as well as a selectable marker gene that confers resistance to an antibiotic (to aid in cloning procedures) and may comprise other sequences to assist in the production and/or secretion of the peptides, such as signal peptide sequences. An example of such a vector is provided by U.S. Pat. No. 5,592,908, to Pavla, which is hereby incorporated by reference in its entirety. Briefly, this patent discusses several known promoters that function in *Lactobacillus* species, as well as a method for discovering novel promoters in said bacteria, any of which may be operably linked to a nucleic acid encoding a peptide of the present invention to express the peptide in Lactobacilli. A nucleic acid encoding a signal peptide, such as peptides comprising of 16 to 35 mostly hydrophobic amino acids that are active in *Lactobacillus lactis* described in U.S. Pat. No. 5,529,908, cited above, is interposed between the promoter and the nucleic acid encoding the peptide of the present invention such that the nucleic acid encoding the signal peptide is in frame with the nucleic acid encoding the peptide of the present invention.

In addition to the coding sequence of the peptide, the DNA sequence synthesized may comprise sequences to aid in the ligation and cloning of said DNA into the expression vector. For example, restriction enzyme recognition sites that correspond to ones found in the multiple cloning site of the vector can be incorporated into the synthesized DNA at the 5' and 3' ends of the sequence, so that the sequence can be cloned in proper orientation within the vector. Both the vector and the synthesized DNA are digested with the particular restriction enzymes, then purified. Ligation reactions with the vector and the synthesized DNA are followed by transformation into a suitable strain of *E. Coli*. The transformed bacteria are plated on media containing the antibiotic to which the vector confers resistance. A colony of transformed bacteria is selected for growth cultures and plasmid preparation procedures; the presence of the synthesized DNA in the correct orientation is confirmed.

This expression vector is then transformed into a bacterial host cell of a *Lactobacillus* species, such as *L. acidophilus*. Transformed cells are selected for by virtue of the selectable marker found within the vector sequence and the secretion of the peptide may be verified by performing a western blot, performing gel electrophoresis of peptides present in the growth medium or other standard techniques. A transformed colony of bacteria is chosen and used to prepare large-scale cultures of the genetically engineered bacteria. A culture of the genetically engineered bacteria expressing the desired peptide is grown up and at least a portion thereof is administered to the alimentary canal, vagina, trachea or other area of the host organism in which the bacteria are able to replicate. If desired, the bacterial cultures can be treated in a variety of ways to produce a supplement for enteric consumption by the host. These treatments include lyophilization or other methods of preserving the bacteria, in addition to combining the bacteria with carrier agents, such as solutions, solvents, dispersion media, delay agents, emulsions and the like. The use of these agents to prepare supplements is well known in the art. For example, the bacteria can be used to make cultured milk products or other foodstuffs for human consumption, such that the organism expressing the peptide colonizes the gut of the host organism. A number of different methods for incorporating specific strains of lactic acid bacteria into foodstuffs such as yogurt, kimchee, cheese and butter are disclosed in U.S. Pat. No. 6,036,952, to Oh, which is hereby incorporated by reference in its entirety. Upon consuming the bacteria through one of any number of routes, the engineered organisms can colonize the gut and allow the presentation and/or absorption of the peptides of this invention via the mucosal layer of the gut.

EXAMPLE 13

Delivery of Peptides Through a Genetically Engineered Form of *Bacillus subtilis*

The following is provided as another exemplary method to deliver peptides of this invention to a host as described above. A DNA sequence that encodes one of the peptides listed in table A above is synthesized by chemical means and this DNA sequence is inserted into an expression vector via techniques of genetic engineering, all techniques being known in the art. The expression vector selected comprises a shuttle vector, such as pTZ18R (Pharmacia, Piscataway, N.J.), capable of being propagated in both *E. Coli* and *B. Subtilis* and containing an antibiotic resistance gene for selecting colonies of transformed bacteria. This vector can contain a constitutive promoter active in *B. subtilis*, such as a promoter derived from the Sac B gene of *B. subtilis* as well as a nucleotide sequence encoding a signal peptide active in *B. subtilis* that directs efficient export of expressed heterologous proteins from the bacterial cell. An example of such a vector is disclosed in U.S. Pat. No. 6,268,169, to Fahnestock, the disclosure of which is incorporated herein by reference in its entirety. Briefly, as detailed above, the DNA encoding a peptide of this invention will be synthesized with restriction enzymes sites and/or other sequences to facilitate cloning of the DNA through techniques familiar to those with skill in the art. After transformation into *E. Coli.*, plating, selection and propagation of the plasmid to create a plasmid stock, the plasmid is then be transformed into *B. subtilis* and transformants are selected by virtue of resistance to an antibiotic in the plating media.

Peptide production in and secretion from the genetically engineered *B. subtilis* is verified using techniques well known to those with skill in the art, such as radiolabeling of peptides for autoradiographic detection after SDS-PAGE analysis or Western blotting.

A culture of genetically engineered bacteria is grown up and at least a portion thereof is administered to the alimentary canal, vagina, trachea or other area of the host organism in which the bacteria are able to replicate.

EXAMPLE 14

Delivery of Peptides Through Genetically Engineered *Saccharomyces Yeast Species*

The following is provided as another exemplary method to deliver peptides of this invention to a host as described above. A DNA sequence that encodes one of the peptides listed in table A above is synthesized by chemical means and this DNA sequence is inserted into an expression vector via techniques of genetic engineering, all techniques being known in the art. The expression vector selected comprises a stably maintained yeast protein expression vector, comprising a constitutive yeast promoter such as pADH1, sites for replication of the vector in both yeast and *E. Coli*, a gene or genes that confer prototrophy to an auxotrophic yeast mutant for selection purposes, a multiple cloning site (MCS) and, if desired, sequences that code for a signal peptide. Vectors such as this are commercially available and well known in the art or can be readily constructed using standard techniques After insertion of the synthesized DNA into the yeast vector, transformation into *E. Coli*, plating of transformed *E. Coli* onto selective media, selection of a transformed bacterial colony and preparation of plasmid DNA from a growth culture of bacteria from said colony, the vector is transformed into *Saccharomyces cerevisiae* via well-known techniques such as lithium acetate transformation or electroporation. The strain of *Saccharomyces cerevisiae* selected for transformation is a mutant auxotrophic strain that will require a gene on the plasmid in order to grow on minimal media plates. Transformed yeast colonies are isolated by plating the yeast on growth media lacking the gene provided on the vector. Only those yeast that have received the vector and its selective gene and are expressing that gene product will be able to grow into colonies on the minimal media. Verification of peptide secretion can be obtained by performing a Western blot, performing gel electrophoresis of peptides present in the growth medium or other standard techniques.

A transformed colony of yeast is chosen and used to prepare large scale cultures. A culture of the genetically engineered yeast expressing the desired peptide is grown up and at least a portion thereof is administered to the alimentary canal, vagina, trachea or other area of the host organism in which the bacteria are able to replicate. If desired, the yeast cultures can be treated in a variety of ways to produce a supplement for enteric consumption by the host. These treatments include lyophilization or other methods of preserving yeast, in addition to combining the bacteria with carrier agents, such as solutions, solvents, dispersion media, delay agents, emulsions and the like. The use of these agents to prepare supplements is well known in the art. In another embodiment, the transformed yeast are used in the creation of food products, such as fermented milk products like yogurt and kefir, by techniques known to those skilled in the art. As with live lactic acid bacterial cultures in these foodstuffs, the transformed yeast colonize the gut at least transiently and serve to present peptides to the host via the gut lumen.

While the present invention has been described using the aforementioned methods and data and the specific example of the peptides described herein in many cases, it is understood that this is an example only and should not be taken as limitation to the present invention. It should also be understood that these peptides described herein represent some embodiment of the present invention and the same principle of the present invention can also apply to other functionally equivalent peptides that have been modified without affecting the biological function of these peptides. Furthermore, although the disease or disorder described above for the medical application of these peptides are recited to support their usefulness, these medical applications are used as non-limiting examples only and should not be used to limit the scope of the claims. It is clear that there are other possible/intended use of these peptides and their functional derivatives, such as but not limited for use as a health food supplement to enhance or boost the immune system, alleviate fatigue, reduce blood lactic acid of a normal person or a patient with any infections. Any such uses also fall within the scope of the present invention.

As for the peptides with sequences that have been previously published, the present invention has provided new and unexpected uses therefor, and it is believed that these new indication support the use of some of these know peptides for industrial applications that were previously unforeseen. Beside new medical uses as described above and in the claims, they can also be used as dietary or nutritional supplements for improving conditions of a normal individual based on the teaching provided herein.

What is claimed is:

1. A method of increasing liver glycogen storage level in a patient in need thereof comprising administering a pharmaceutically effective dose of a biologically active peptide, said biologically active peptide having the amino acid sequence consisting of SEQ ID NO: 1.

* * * * *